(12) United States Patent
Chappel

(10) Patent No.: US 8,790,318 B2
(45) Date of Patent: Jul. 29, 2014

(54) MICROMECHANIC PASSIVE FLOW REGULATOR

(75) Inventor: Eric Chappel, Versonnex (FR)

(73) Assignee: Debiotech S.A., Lausanne (CH)

(*) Notice: Subject to any disclaimer, the term of this patent is extended or adjusted under 35 U.S.C. 154(b) by 0 days.

(21) Appl. No.: 13/578,711

(22) PCT Filed: Feb. 7, 2011

(86) PCT No.: PCT/IB2011/050514
§ 371 (c)(1),
(2), (4) Date: Aug. 13, 2012

(87) PCT Pub. No.: WO2011/098946
PCT Pub. Date: Aug. 18, 2011

(65) Prior Publication Data
US 2012/0316492 A1 Dec. 13, 2012

(30) Foreign Application Priority Data

Feb. 12, 2010 (EP) .................................... 10153449

(51) Int. Cl.
F16K 1/42 (2006.01)
(52) U.S. Cl.
USPC ................... 604/288.04; 137/625.3; 137/503; 251/61.1; 251/205
(58) Field of Classification Search
USPC ........... 251/61, 61.1, 205, 206, 331; 137/497, 137/500, 503, 504, 505.13, 510, 625.3, 137/625.4; 604/891.1, 9, 288.04
See application file for complete search history.

(56) References Cited

U.S. PATENT DOCUMENTS 5,839,467 A * 11/1998 Saaski et al. ................. 137/501
6,276,491 B1 * 8/2001 Schonfeld .................... 137/503

(Continued)

FOREIGN PATENT DOCUMENTS

DE 42 23 067 A1 1/1994
DE 102005058080 6/2007

(Continued)

OTHER PUBLICATIONS

International Search Report for PCT/IB2011/050514, mailed May 30, 2011.

(Continued)

Primary Examiner — Eric Keasel
(74) Attorney, Agent, or Firm — Nixon & Vanderhye P.C.

(57) ABSTRACT

The invention concerns a flow regulator, made of a stack of 3 plates, respectively a top plate including a flexible membrane (1), a middle plate (2) with pillars and through holes and a bottom plate (3) with fluidic ports, micro channels and through holes (8,9,12). The principle is based on the deformation of the membrane due to the pressure of the liquid. The membrane goes in contact with the pillars of the middle plate, obstructing gradually the through holes of the pillars. The device is designed to keep the flow constant in a predefined range of pressure. The device is dedicated to ultra low flow rate up to 1 ml per day or below, typically for drug infusion. Plastic flow regulators comprise preferably several independent valves coupled in parallel. The membrane plate is therefore made of several flexible membranes obstructing gradually the flow by increasing the pressure. Stress limiters are used to avoid plastic deformation of the membrane. For implanted pump, the use of a flow regulator instead of a flow restrictor has several advantages, including the possibility to reduce significantly the reservoir pressure and to generate directly the pressure during the pump filling by using an elastic drug reservoir.

19 Claims, 19 Drawing Sheets

(56) References Cited

U.S. PATENT DOCUMENTS

| | | | |
|---|---|---|---|
| 6,986,365 B2 * | 1/2006 | Henning et al. | 137/625.3 |
| 8,539,981 B2 * | 9/2013 | Chappel | 251/61.1 |
| 2005/0054988 A1 | 3/2005 | Rosenberg et al. | |
| 2006/0206049 A1 | 9/2006 | Rodgers et al. | |
| 2008/0154215 A1 | 6/2008 | Rosenberg et al. | |
| 2008/0249510 A1 | 10/2008 | Mescher et al. | |
| 2010/0028170 A1 | 2/2010 | Schneeberger et al. | |
| 2010/0324504 A1 | 12/2010 | Chappel et al. | |

FOREIGN PATENT DOCUMENTS

| | | |
|---|---|---|
| EP | 0 369 712 A2 | 5/1990 |
| WO | WO 2010/020891 | 2/2010 |

OTHER PUBLICATIONS

Written Opinion for PCT/IB2011/050514, mailed May 30, 2011.
European Search Report dated Aug. 17, 2010—issued in corresponding European Patent Application No. EP 10153449.3 that corresponds to PCT/IB2011/050514.

* cited by examiner

MICROMECHANIC PASSIVE FLOW REGULATOR

This application is the U.S. national phase of International Application No. PCT/IB2011/050514 filed 7 Feb. 2011 which designated the U.S. and claims priority to EP Patent Application No. 10153449.3 filed 12 Feb. 2010, the entire contents of each of which are hereby incorporated by reference.

FIELD OF THE INVENTION

The present invention relates to fluid flow regulators used in the field of drug delivery, the drug being either liquid or gaseous, for instance for pain management. Such flow regulators can also be used for draining cerebrospinal fluid (CSF) for hydrocephalus patient. The invention further relates to fabrication processes of such flow regulators.

STATE OF THE ART

Passive drug infusion devices, in contrast to active ones, do not rely on a pump to deliver a drug but rather on a pressurized drug reservoir. A known problem of these passive devices is that the drug flow rate to a delivery location, which may be a patient's body for instance, may vary as a function of the amount of drug remaining in the reservoir as far as the pressure in the reservoir depends on this amount. Such passive devices are thus usually provided with a fluid flow regulator to ensure that the drug flow rate is as constant as possible with respect to the amount of drug remaining in the reservoir.

An example of such a passive drug flow regulator is available by the Applicant under the registered name "Chronoflow" and is disclosed in U.S. Pat. No. 6,203,523 B1. This device comprises a fluid inlet adapted to be connected to a fluid reservoir and a fluid outlet adapted to be connected to a patient's body. It comprises a rigid substrate and a resilient membrane tightly linked together in peripheral linking areas so as to define a cavity therebetween. This cavity is connected to the fluid outlet while the membrane has a first surface opposite the cavity which is connected to the fluid inlet. The membrane has a central through hole contiguous with the cavity, to define a pathway for a fluid from the fluid inlet to the fluid outlet, and is flexible so as to be able to come into contact with the substrate, in case a fluid would apply a pressure on the first surface that would be larger than a first predefined threshold value. As the membrane would come into contact with the substrate in the region of its central through hole, this would occlude the latter and result in hindering a fluid from flowing through it.

This device further comprises a flow regulator open channel etched in the substrate with an inlet facing the central through hole of the membrane and an outlet connected to the outlet of the device. This channel is in the shape of a spiral curve such that, the more pressure is applied against the membrane, the more it closes the channel thus forcing the fluid to flow in it to find its way out of the cavity.

Consequently, when the pressure applied on the membrane increases, the length of the fluid pathway located within the flow regulator channel increases and so does the fluidic resistance of the device. Thus, the flow rate may be kept approximately constant within a predefined range in terms of the reservoir pressure.

However, fabrication of such a device is complicated and expensive. Indeed, the substrate has to be etched according to a specific pattern, which is rather delicate regarding the accuracy level that has to be respected for the flow regulation to operate properly. Thus, not only the manufacture of the substrate requires specific extra-steps, but also these steps are further delicate to carry out. Depending on the dimensions of the device, specific materials such as SOI is to be used for manufacture of the substrate, which is still more expensive. It is also important to note that this device is sensitive to particles. The large contact area between the membrane and the substrate at high pressure can be problematic since any particle in this area will induce a leakage.

Moreover, the device manufactured through this process is then designed for one specific set of parameters regarding delivery of a drug, i.e. predefined reservoir pressure range and average flow rate. Complex fluidic simulations of such device are necessary to estimate the spiral shape and to take into account the flow restriction outside of the channel, making any design change difficult.

Park reports another constant flow-rate microvalve for hydrocephalus treatment [S. Park, W. H. Ko, and J. M. Prahl, "A constant flow-rate microvalve actuator based on silicon and micromachining technology," in Tech. Dig. 1988 Solid-State Sens. Actuator Workshop (Hilton Head '88), Hilton Head Island, S.C., Jun. 6-9 (1988) 136-139]. The valve is also made of a diaphragm covering a flat substrate; the channel cross-section diminishes under increasing pressure, thus leading to quasi-steady flow-rate. Both theoretical and experimental data reported show that a perfectly steady rate cannot be achieved since the flow resistance should increase with the applied pressure in a linear manner and the change of the cross-section of the channel is strongly non-linear. This non-linearity is not compensated by the use of a spiral channel. All limitations discussed for the design described in U.S. Pat. No. 6,203,523 B1 are present here.

Kartalov reports a PDMS-based device for passive flow regulation of Newtonian fluid [E. P. Kartalov, C. Walker, C. R. Taylor, W. F. Anderson, and A. Scherer, "Microfluidic vias enable nested bioarrays and autoregulatory devices in Newtonian fluids," Proc. Nat. Acad. Sci. 103 (2006) 12280-12284]. This device is made of a three-dimensional structure showing an important dead volume. The autoregulated device comprises a main channel between a source and an exhaust, the static pressure decreases as the fluid flows along this channel which also comprises a flexible membrane called pushup valve. The static pressure remains constant along the dead-end detour channel leading to the valve. The pushup valve experiences an effective pressure equal to the static pressure drop between the channel split and the main channel segment above the valve. As the pressure drop increases, the valve membrane deforms upward and constricts the main channel, leading to an increase of the fluidic resistance with applied pressure and thus to nonlinearity for Newtonian fluids. The presence of dead-ends for such devices makes the priming difficult. Air trapped below the valve would induce damping effect. But the main drawback of such devices is the flow-rate accuracy. The use of plastic parts is very attractive in terms of cost but it seems very difficult to achieve a controlled deflection of the valve in order to get a constant flow rate. For high modulus plastic, the membrane will experience non-linear and thus plastic deformation during overpressure, leading to irreversible damages. In any case, the change of the cross-section of the channel is strongly non-linear and the device cannot achieve, by design, a constant flow-rate. Moreover, and according to the Poiseuille's law, it is difficult to match the fabrication tolerances of plastic microchannels and membranes to the flow rate accuracy expected for medical infusion of drugs.

Microfluidic autoregulation using the non-Newtonian rheological properties of concentrated polymeric solutions have been reported by Groisman [Groisman et al., (2003) Science 300, 955-958]. For medical application, one of the main limitations of such device is the use of biocompatible polymer solution.

A passive flow regulator that exploits the large compliance of elastomeric polymers has been proposed by Yang [B. Yang and Q. Lin, A Planar Compliance-Based Self-Adaptive Microfluid Variable Resistor, Journal of microelectromechanical systems 16 (2007) 411-419]. The device comprises a thin flap and a stiff stopper. The gap between the flap and the stopper varies with the applied pressure, resulting in a non-linear resistance. Constant flow-rates of 0.21 ml/min and 1.2 ml/min between 100 and 200 kPa have been obtained for two different devices using DI water. Here again, we do not expect high reproducibility and accuracy from one device to another because of the plastic fabrication tolerances. This limitation is particularly problematic at low flow-rate, typically below 1 ml per hour.

Saaski et al. disclose in U.S. Pat. No. 5,839,467 a device having a membrane tightly attached to a substrate that have a cavity and a central pillar having a through hole. The inlet is located on the lateral side of the substrate. The fluid flows from this inlet towards the outlet located after the through hole of the substrate pillar. The membrane side opposite to the pillar is submitted to the reservoir pressure. The small gap between the upper part of the pillar and the membrane forms a large fluidic restriction. By increasing the reservoir pressure the membrane deflects towards the pillar, reducing the gap height between the pillar and the membrane. The device can be considered as a valve which can shut off when the reservoir pressure increases, i.e. when the gap height between the pillar and the membrane becomes equal to zero. In that case, the pressures on both sides of the membrane are equal excepted above the pillar area. Various configurations including check-valve feature, shut-off feature, device having a membrane with a through hole and a non-drilled pillar are disclosed. For each proposal, the flow rate can be therefore more or less controlled up to the closing of the valve but in any case a constant flow rate can be achieved because of the non-linearity of the fluidic resistance of that valve as the gap height varies. Moreover, the fact that the reservoir pressure applies directly on both sides of the membrane makes necessary the use of a small gap between the pillar and the membrane at any pressure otherwise the device do not regulate the flow. The gap 48 disclosed of only 2.5 microns (FIG. 6) is an illustration of this feature. The device is therefore very sensitive to particles. Relative machining tolerances for this gap are also difficult to achieve.

Patent application WO2008/094672A2 discloses capacitive type fluidic valves made of several layers and comprising lateral ports, a flexible membrane and a substrate having a pillar with a hole. By changing the fluid pressure the membrane deflects towards the pillar and increases the fluidic resistance of the valve. Only one side of the membrane is in contact with the fluid. The fluid can flow up to the valve via channels directly machined or formed in the substrate plate. These channels shall not exhibit a fluidic resistance of the same order of magnitude of that of the valve itself otherwise the damping effect due to the membrane deflection is no longer efficient. The non-linearity of the membrane deflection with the fluid pressure prevents the possibility to reach a constant flow rate or a flow rate having a specific profile over a given range of pressure.

Patent application DE4223067A1 discloses a device having lateral fluidic ports, one flexible membrane that comprises one pillar having one through hole. The functioning principle is very similar to the previous example of flow regulators and therefore the device shows the same limitations in term of accuracy.

Patent application FR2905429 discloses a device having resilient polymeric membrane as a part of a reservoir and also as part of a valve or two separated resilient membranes for the reservoir and the valve, a substrate having a hole and a pumping mechanism. The resilient membranes show no opening. The valve disclosed in the document has an anti-free flow function and therefore the membrane should comply with the valve seat to ensure tightness. This compliance is not compatible with the possibility to regulate the flow according to a specific profile because rigid membrane is necessary.

To summarize the state-of-the-art, we can point out that all devices are not adapted to flow rate lower than 1 ml per hour because the fabrication tolerances and the designs themselves strongly limit the flow rate accuracy, making the device not suitable for medical use. Passive regulators disclosed in the patents U.S. Pat. No. 6,203,523 B1 and WO 2,009,098,314 A1 are preferably made in silicon. The designs are based on a non-linear deformation of an elastic membrane and therefore silicon is used as membrane thanks to its high yield strength and low internal stress.

A new design adapted to the use of other materials like plastics for the membrane is desirable.

Passive flow regulators may advantageously be used in hydrocephalus treatment. Hydrocephalus is usually due to blockage of CSF outflow in the ventricles or in the subarachnoid space over the brain. Hydrocephalus treatment is surgical: it involves the placement of a ventricular catheter (a tube made of silastic for example) into the cerebral ventricles to bypass the flow obstruction/malfunctioning arachnoidal granulations and the draining of the excess fluid into other body cavities, from where said fluid can be resorbed. Most of the CSF shunts have been based on the principle of maintaining a constant intracranial pressure (ICP) regardless of the flow-rate of CSF. The CSF shunts have been constructed to cut off CSF-flow when the differential pressure between the inlet and the outlet of the CSF shunt was reduced to a predestined level, called the opening pressure of the shunt. An example of an ICP shunt is shown in U.S. Pat. No. 3,288,142 to Hakim, which is a surgical drain valve device used to control the drainage of fluid between different portions of the body of a patient, particularly for draining cerebrospinal fluid from the cerebral ventricles into the blood stream (co called ventriculo-atriostomy).

Clinical experience has proven that this principle of shunting is not an ideal solution. Sudden rises of the ICP, e.g. due to change of position, physical exercise, or pathological pressure waves result in excessive CSF drainage. Several reports in the literature (Aschoff et al., 1995) point at problems due to this overdrainage, and especially the pronounced narrowing of the ventricles has been pointed out as being the main factor leading to malfunctioning of the implanted shunting device. The reason is that the ventricular walls may collapse around the ventricular CSF shunt device, and particles (cells, debris) may intrude into the shunt device. U.S. Pat. No. 5,192,265 to Drake et al. describes an example of a shunt seeking to overcome the above-mentioned difficulties by proposing a rather complex anti-siphoning device allowing to select transcutaneously the resistance to flow by controlling the pressure in a chamber gas-filled and being in pressure communication with one flexible wall of the main chamber where the flow is regulated.

The use of programmable valves was associated with a reduction in the risk of proximal obstruction and overall shunt revision, one possible explanation for a difference in the two populations studied is that programmable valves may allow the physician to avoid such ventricular collapse by increasing the valve pressure setting after noting clinical signs and symptoms and/or radiological evidence of overdrainage. In this way, proximal obstruction is prevented, and shunt revision surgery is avoided. One such adjustable valve is described in U.S. Pat. No. 4,551,128 to Hakim et al. However, due to the elastomeric properties of the diaphragm material, maintenance of the implanted valve may be required. Further, flow rate adjustment of this adjustable valve after implantation may require a surgical procedure.

Another adjustable valve mechanism, described in U.S. Pat. No. 4,781,673 to Watanabe, includes two parallel fluid flow passages, with each passage including a flow rate regulator and an on-off valve. Fluid flow through the passages is manually controlled by palpably actuating the on-off valves through the scalp. Although the Watanabe device permits flow rate control palpably through the scalp and thus, without surgical intervention, patient and/or physician attention to the valve settings is required.

One system, described in U.S. Pat. No. 6,126,628 to Nissels, describes a dual pathway anti-siphon and flow-control device in which both pathways function in concert. During normal flow, both the primary and secondary pathways are open. When excessive flow is detected, the primary pathway closes and flow is diverted to the high resistance secondary pathway. The secondary pathway decreases the flow rate by 90% while maintaining a drainage rate within physiological ranges, which prevents the damaging complications due to overdrainage. However, this device is intended for use with a shunt system including a valve for controlling flow rate and should be placed distal to the valve inducing cumbersome procedure due to the additional material to be implanted. The system can be used as a stand-alone only for low-pressure flow-control valve.

Another application of passive flow regulators is the infusion of drugs. Current implantable pumps for pain management deliver few milliliters per day (Codman®3000, IsoMed®). The system can be pressurized by a gas like a lighter. The gas pushes the drug into a capillary and the flow rate is directly proportional to the difference between the vapour pressure of the gas and the atmospheric pressure. In order to be independent from any change of the atmospheric pressure, the vapour pressure of the gas is typically larger than 2 bars, making the refill procedure rather difficult.

It is therefore desirable to have an easy-to-use and efficient flow regulator dedicated to ultra low flow rate, typically 4 ml per day or below.

Replacing the flow restrictor of current implantable pumps by a flow regulator would allow a significant lowering of the vapour pressure of the gas up to a factor ten or more. This feature would facilitate the pump filling. It is also possible to use a larger set of pressurization systems, including of course the gas propeller system, an elastomeric reservoir that pushes the liquid through the flow regulator, a soft reservoir and a spring that is compressed during the filling of the pump . . . . Finally, the use of a flow regulator would significantly reduce the risk of overdose due to a shock.

GENERAL DESCRIPTION OF THE INVENTION

The aim of the present invention to propose a passive fluid flow regulator that overcomes the above-mentioned drawbacks. Another aim of the present invention is to offset the drawback of the prior art mentioned above by proposing, as an alternative, a passive fluid flow regulator which is easier and cheaper to manufacture and which would provide more flexibility and accuracy as far as its conditions of use are concerned.

To that end, the present invention relates to a flow regulator comprising a fluid inlet adapted to be connected to a fluid reservoir and a fluid outlet adapted to be connected to a delivery location, said regulator comprising a rigid substrate and a flexible membrane tightly linked together in predefined linking areas, said substrate and/or said membrane having a recess so as to define—when said membrane is in a rest position—a cavity between said membrane and said substrate; said substrate and/or said membrane having a through hole contiguous with said cavity and communicating with said fluid outlet, said substrate and/or said membrane furthermore comprising two additional through holes contiguous with said cavity and communicating with said fluid inlet; said substrate and/or said membrane having at least two pillars within said cavity, the height of each of said pillars being such that, when said membrane is at rest, a gap is formed between the pillar free end and the opposite cavity wall; each of said pillars being furthermore aligned with one of said additional through holes and forming a valve in said gap; said pillars furthermore having a width that is larger than the width of said aligned through hole; said flexible membrane being able to come into contact with at least a first part of said substrate, within said cavity and with a portion including a first of said valves, in case a greater pressure than a first predefined threshold value is applied on the surface of the membrane opposite to the said substrate, which results in lowering said gap height up to zero and hindering a fluid from flowing through said first valve, said flexible membrane being able to come into contact with at least a second part of said substrate, within said cavity and with a portion including a second of said valves, in case a pressure larger than a second predefined threshold value is applied on the surface of the membrane opposite to the said substrate, which results in hindering a fluid from flowing through said second valve, wherein the pillars and the additional through holes positions and dimensions are arranged so that the fluid flow rate is passively regulated at least in a range of inlet pressure going from said first and said second predefined threshold values.

Preferred embodiments of the inventions are defined in the dependent claims.

DETAILED DESCRIPTION OF THE INVENTION

The present invention will be better understood at the light of the following detailed description which contains non-limiting examples illustrated by the following figures.

Figure 5:
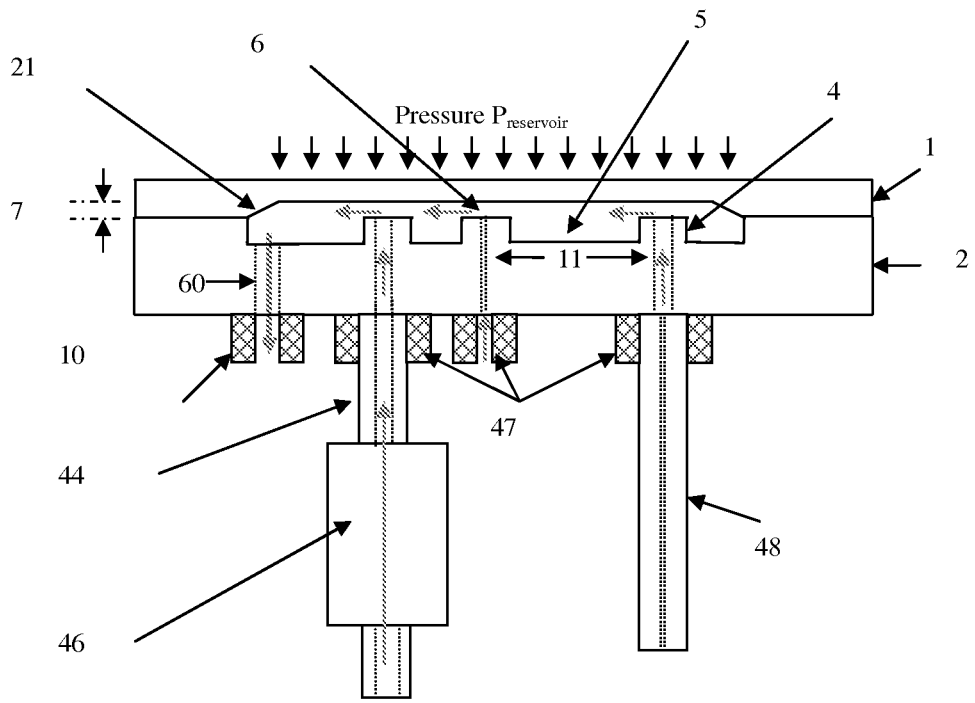

FIG. 5 shows a simplified cross-sectional view of a fluid flow regulator according to another embodiment of the present invention, comprising a membrane plate and a pillar plate, wherein the flow restrictors are located either in the through hole of the pillar plate and/or in a tubing connected to the through hole of the substrate and/or in a dedicated device connected via a tubing to the through hole of the pillar plate.

Figure 6A:
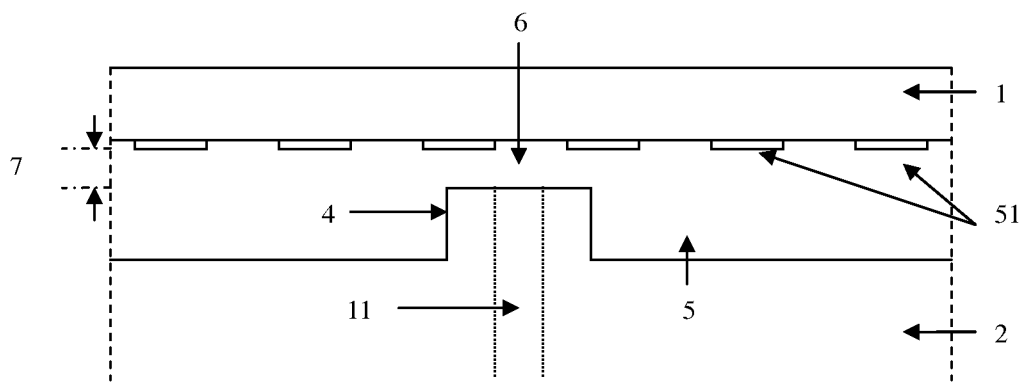

FIG. 6a shows a simplified front-view of a valve according to the first preferred embodiment of the present invention, comprising an anti-bonding layer on the back-side of the membrane.

Figure 6B:
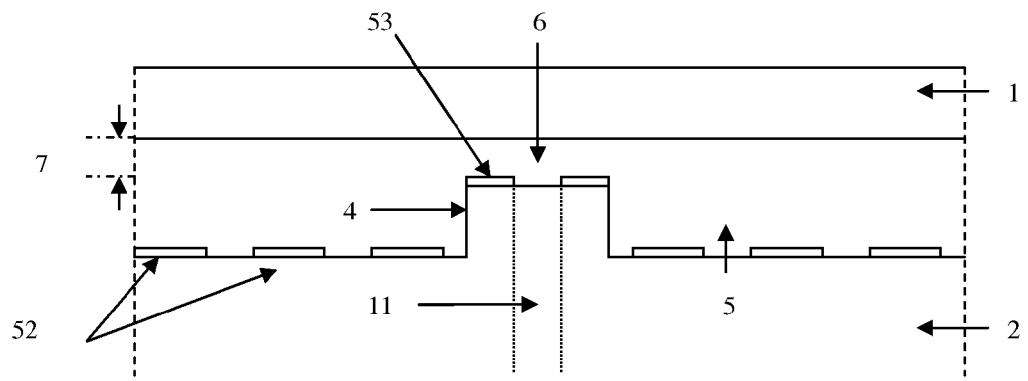

FIG. 6b shows a simplified front-view of a valve according to the first preferred embodiment of the present invention, comprising an anti-bonding layer on the front-side of the pillar plate.

Figure 7A:
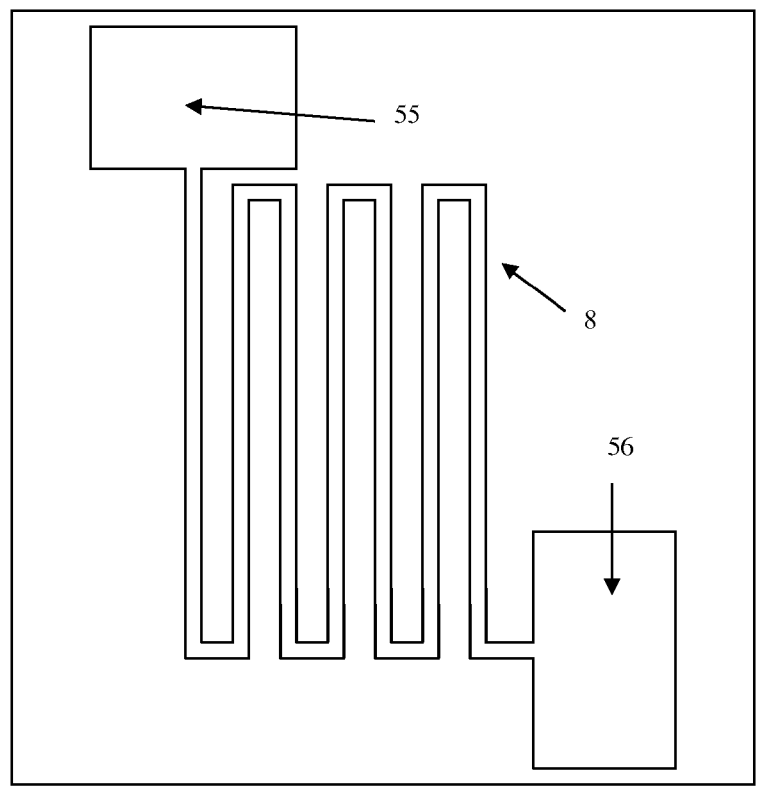

FIG. 7a shows a simplified front-view of a channel machined in either the bottom or the pillar plate.

Figure 7B:
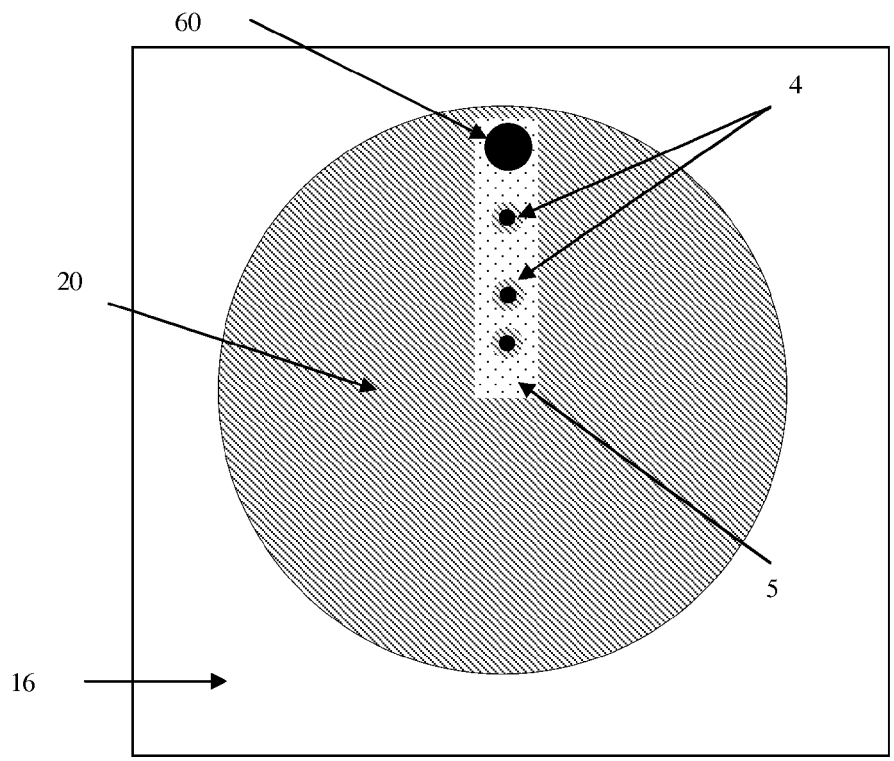

FIG. 7b shows a simplified front-view of a pillar plate according to any of the preceding embodiments of the present invention, comprising a first cavity defining the gap between the pillars and the membrane, and a second cavity defining the height of the pillars.

Figure 8A:
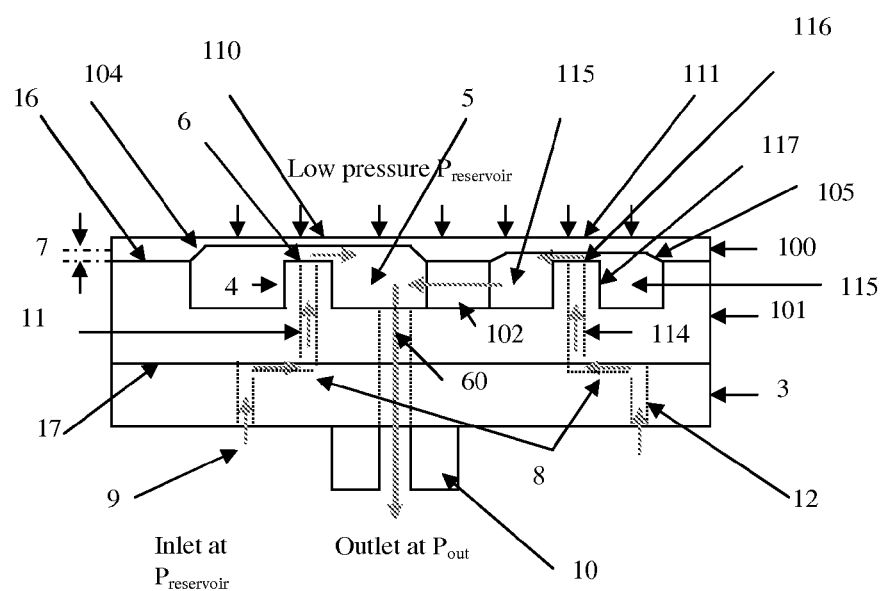

FIG. 8a shows a simplified side-view of the another embodiment of the present invention, the regulator having membranes and gaps of various dimensions and undergoing a first low pressure value.

Figure 8B:
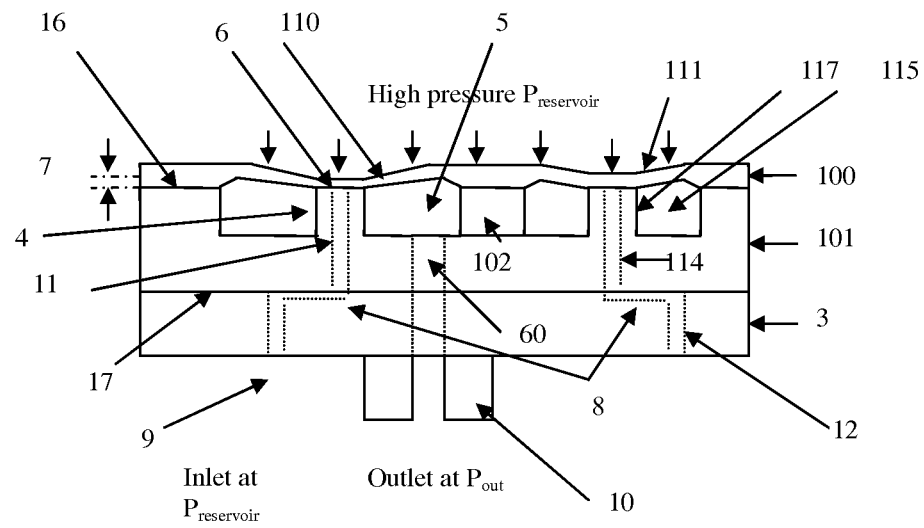
Figure 9A:
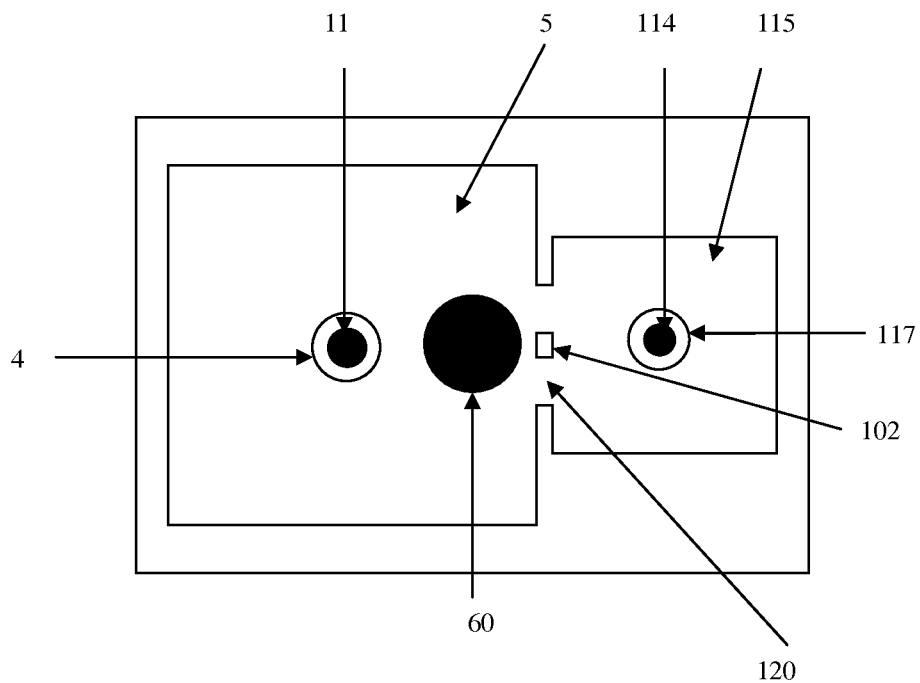

FIG. 8b shows a simplified side-view of another embodiment of the present invention, the regulator having membranes and gaps of various dimensions and undergoing a second larger pressure value;

FIG. 9a shows a simplified front-view of the pillar plate according to another embodiment of the present invention, wherein the pillar cavities are squares and the outlet hole is located between the two pillars.

Figure 9B:
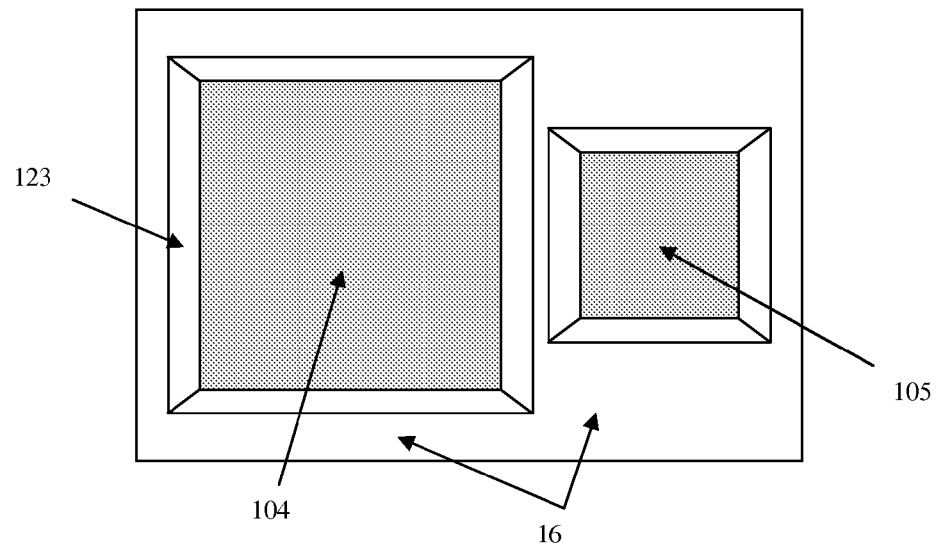

FIG. 9b shows a simplified example of membrane backside (etched side) according to another embodiment of the present invention, wherein the cavities are squares.

Figure 10:
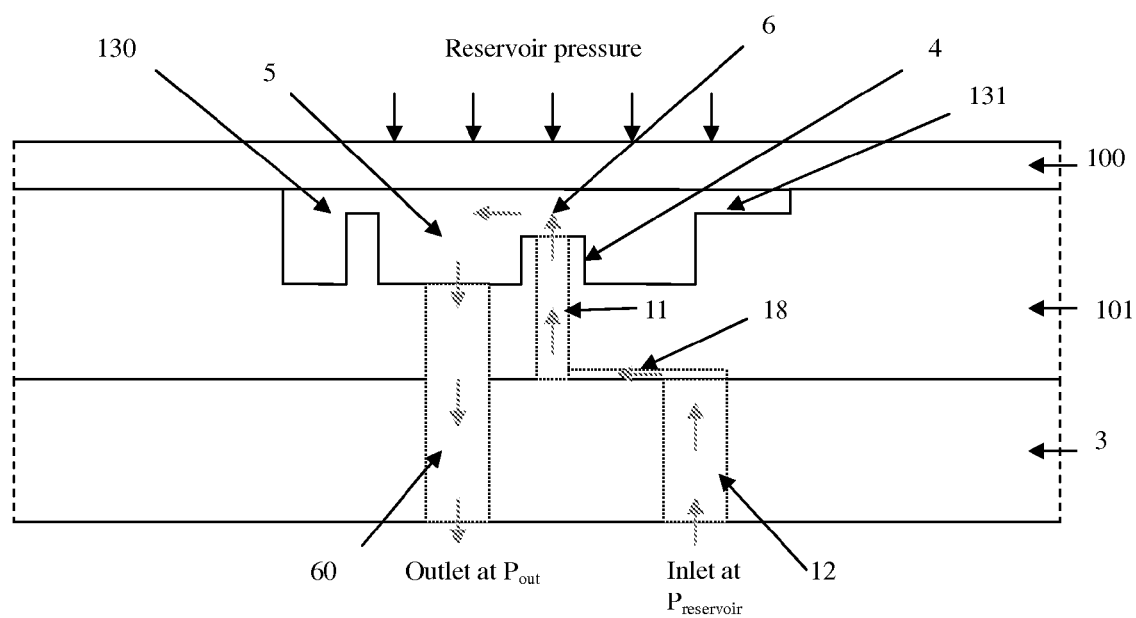

FIG. 10 shows a simplified front-view of a valve according to another embodiment of the present invention, comprising both Stress Limiter Pillars (SLP) and Stress Limiter Steps (SLS).

Figure 11:
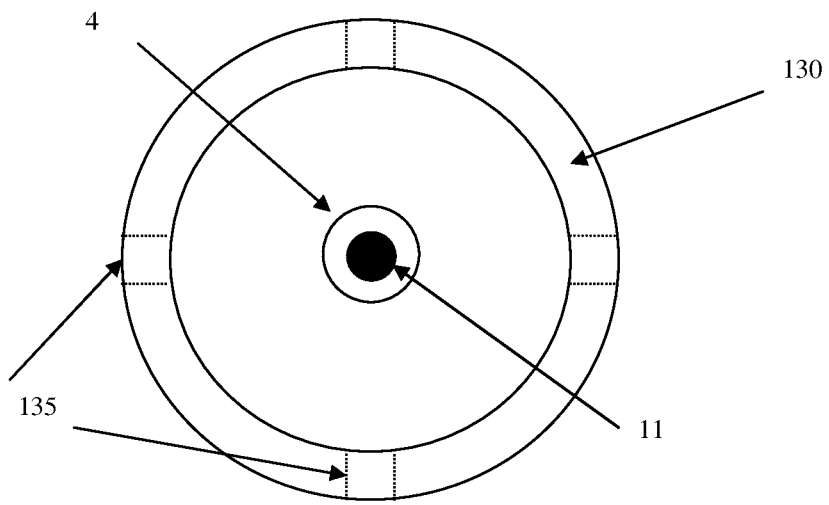

FIG. 11 shows an example of a simplified view of a stress limiter pillar according to another embodiment of the present embodiment.

Figure 12:
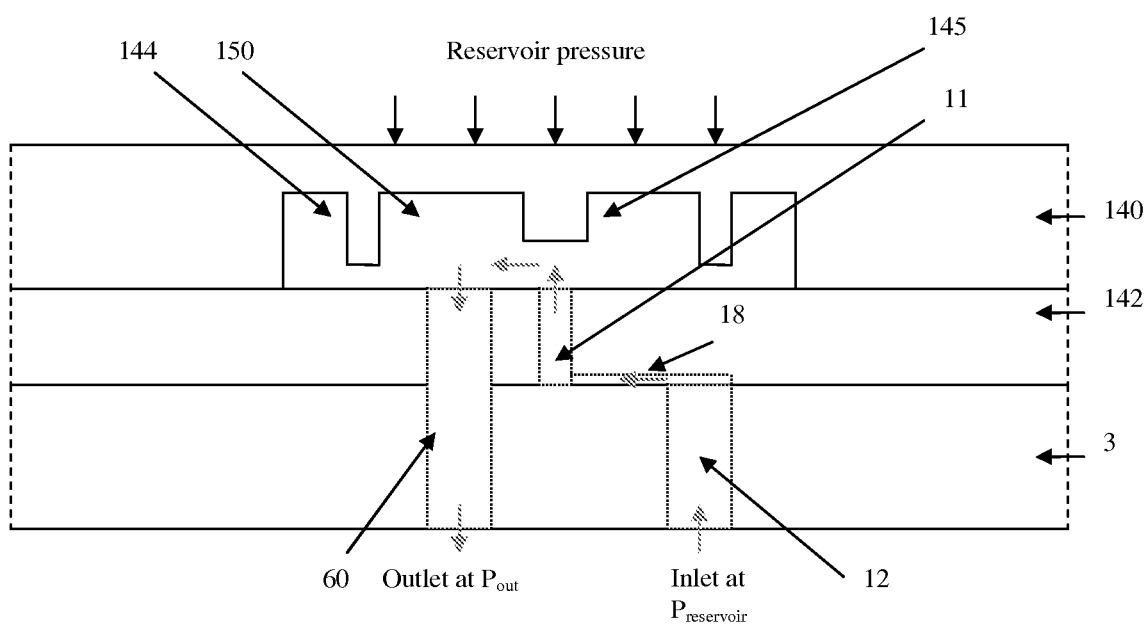

FIG. 12 shows an example of a simplified valve cross-section according to another embodiment of the present invention, wherein the stress limiter pillars and the valve pillars are on the membrane backside.

Figure 13A:
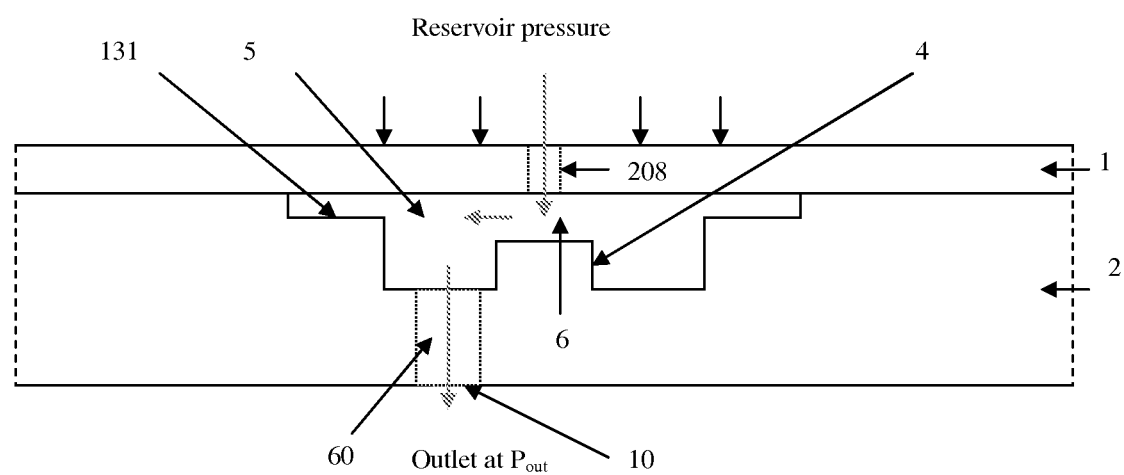

FIG. 13a shows a simplified valve cross-section according to another embodiment of the present invention, wherein the pillar plate comprises stress limiter steps and valve pillar and wherein the membrane has a hole at its centre.

Figure 13B:
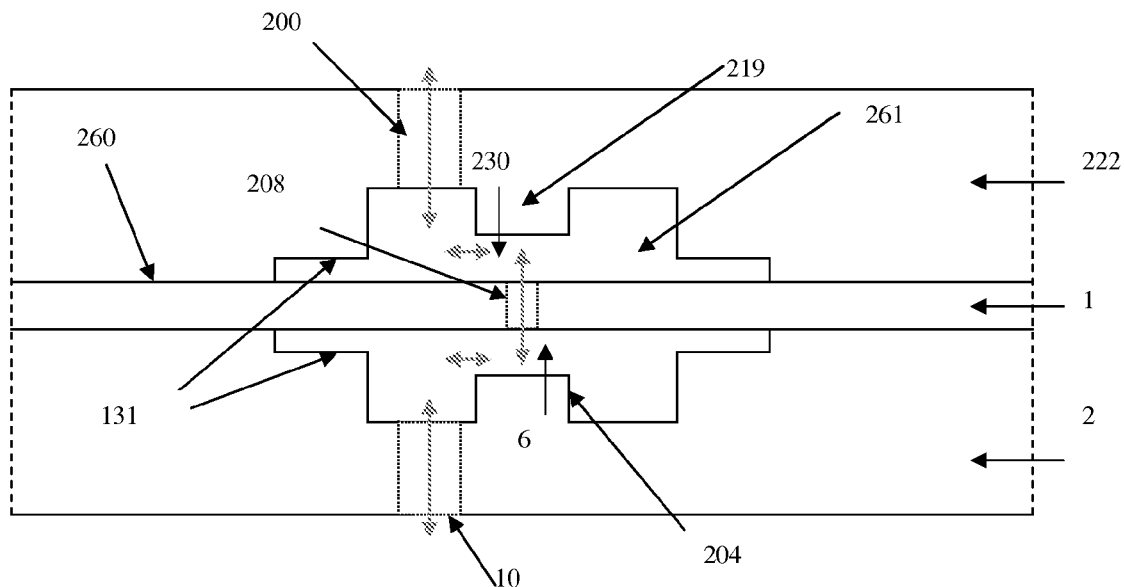

FIG. 13b shows a simplified bidirectionnal valve cross-section according to another embodiment of the present invention, comprising a first pillar plate, a drilled membrane plate and a second pillar plate.

Figure 13C:
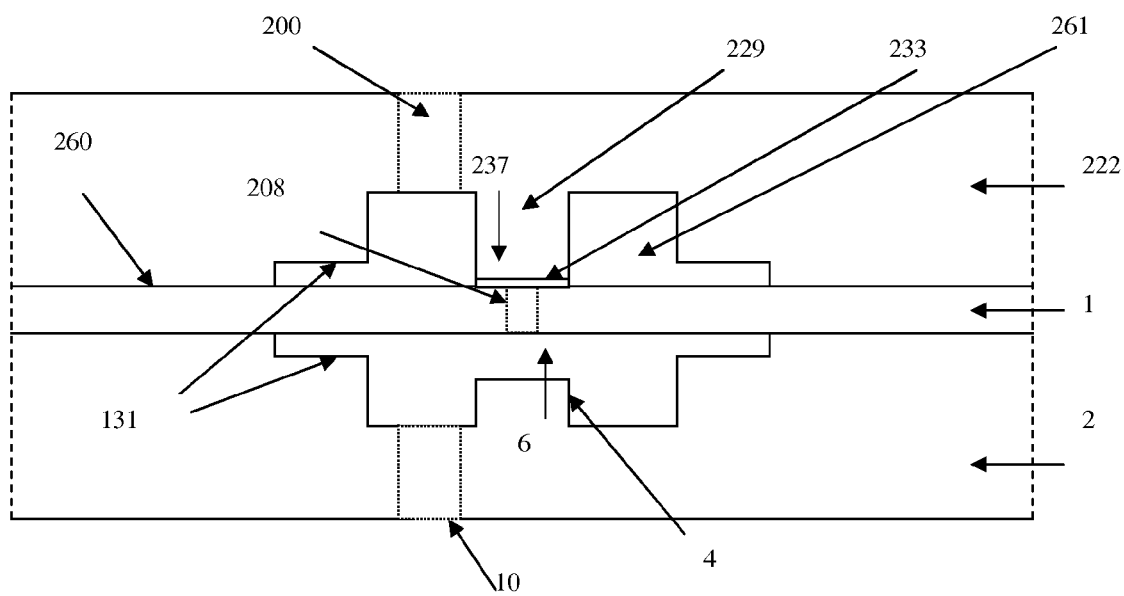

FIG. 13c shows a simplified view of a check-valve cross-section according to another embodiment of the present invention, comprising a first pillar plate having a pillar in contact with the membrane, a membrane plate having a hole and a second pillar plate.

Figure 14A:
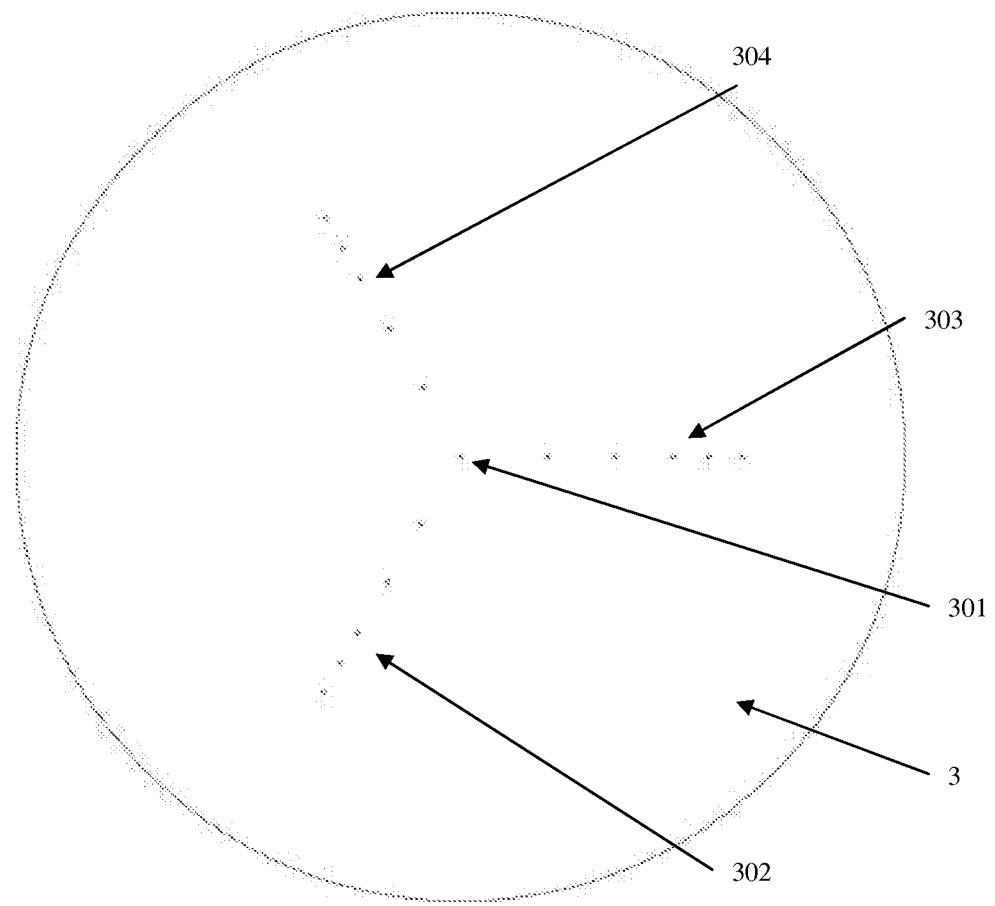

FIG. 14a shows a simplified plan view of a bottom plate or pillar plate backside according to a further exemplary embodiment of the present invention.

Figure 14B:
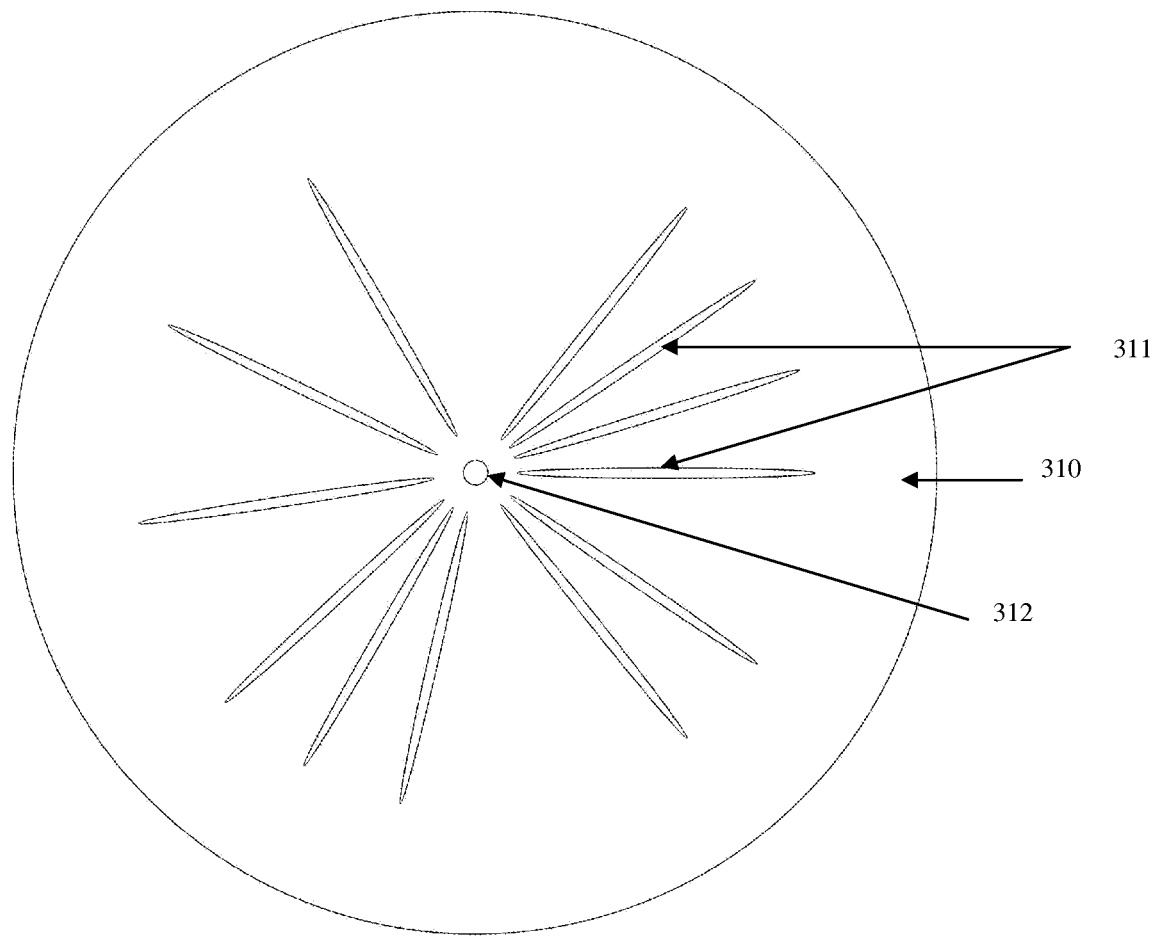

FIG. 14b shows a simplified plan view of a thin film intended to cooperate with the bottom plate or pillar plate backside of FIG. 14a.

Figure 14C:
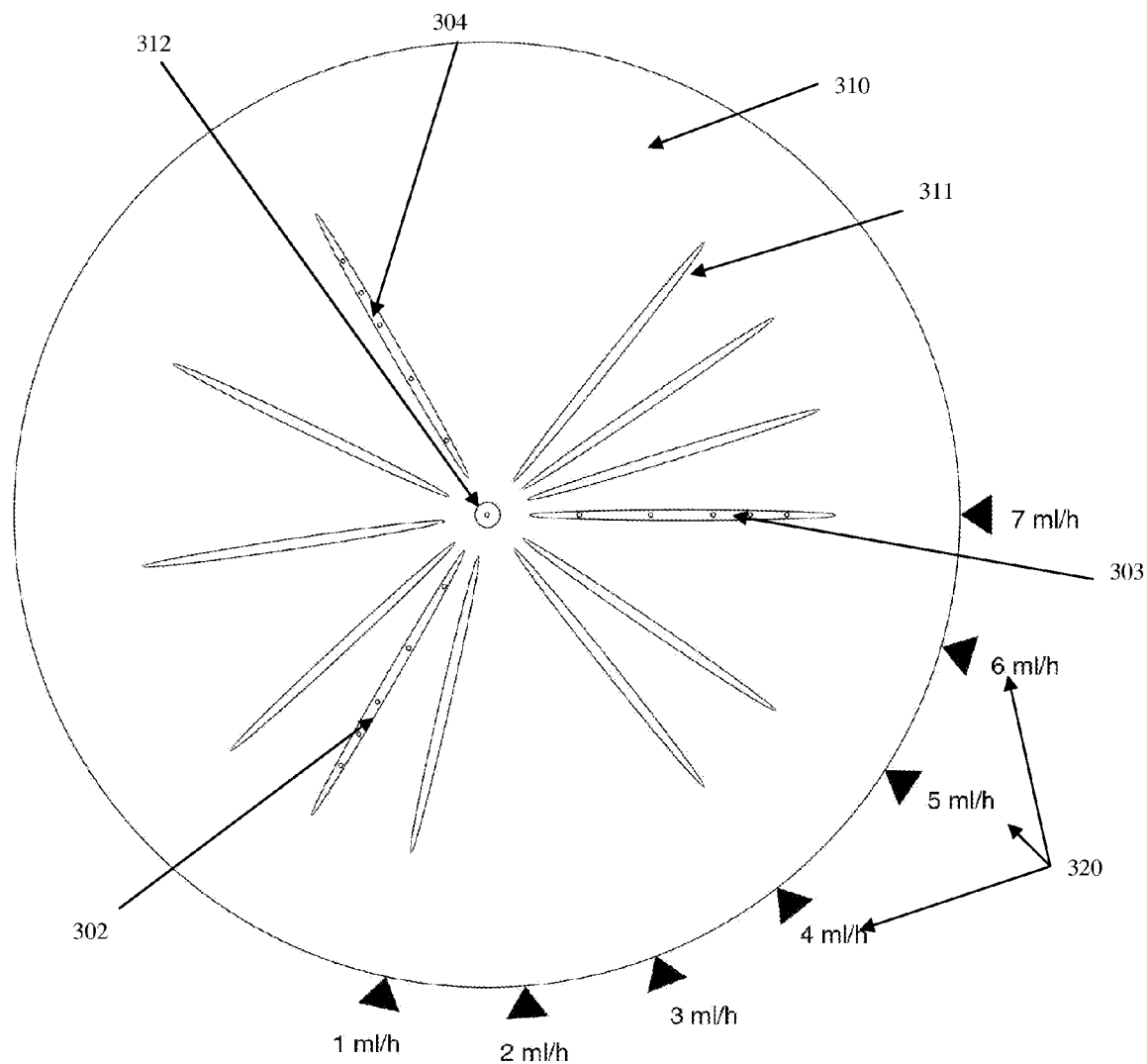

FIG. 14c shows a simplified plan view of the bottom plate or pillar plate backside of FIG. 14a when covered with the thin film of FIG. 14b.

Figure 15A:
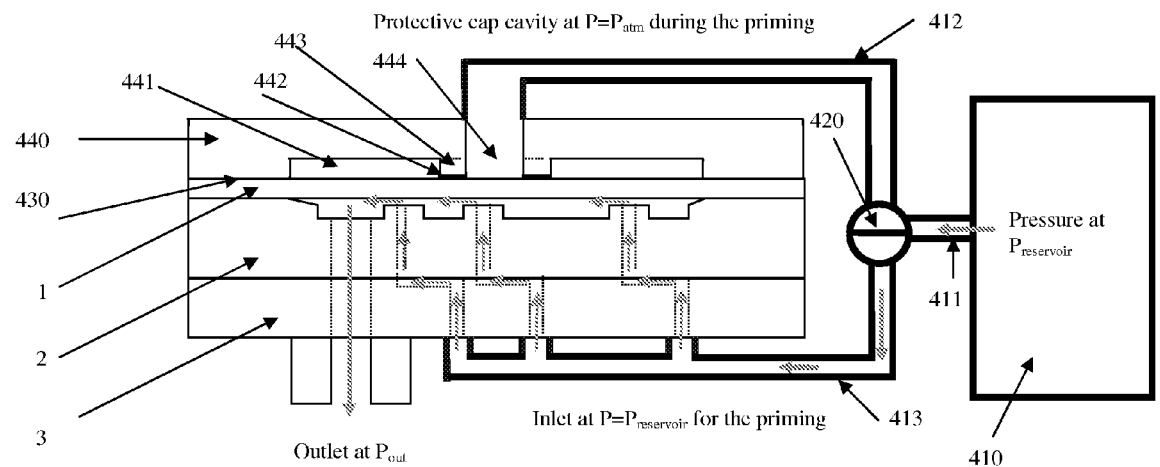

FIG. 15a shows a simplified plan view of the first embodiment of the present invention with additional protective top cap and a fluidic switch in position 1 wherein the pressure is transmitted from the reservoir to only the inlet of the device.

Figure 15B:
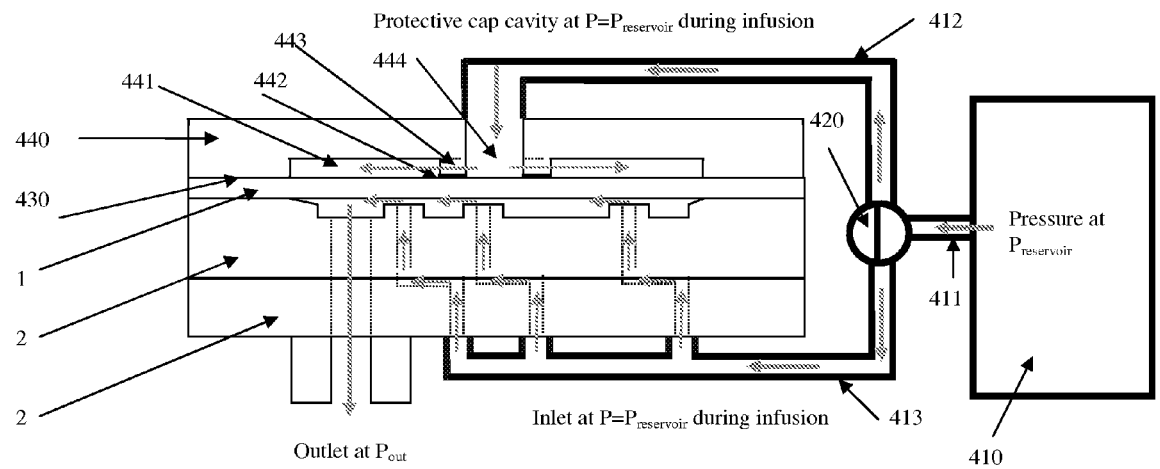

FIG. 15b shows a simplified plan view of the first embodiment of the present invention with additional protective top cap and a fluidic switch in position 2 wherein the pressure is transmitted from the reservoir to both device inlet and protective cap cavity.

Figure 16:
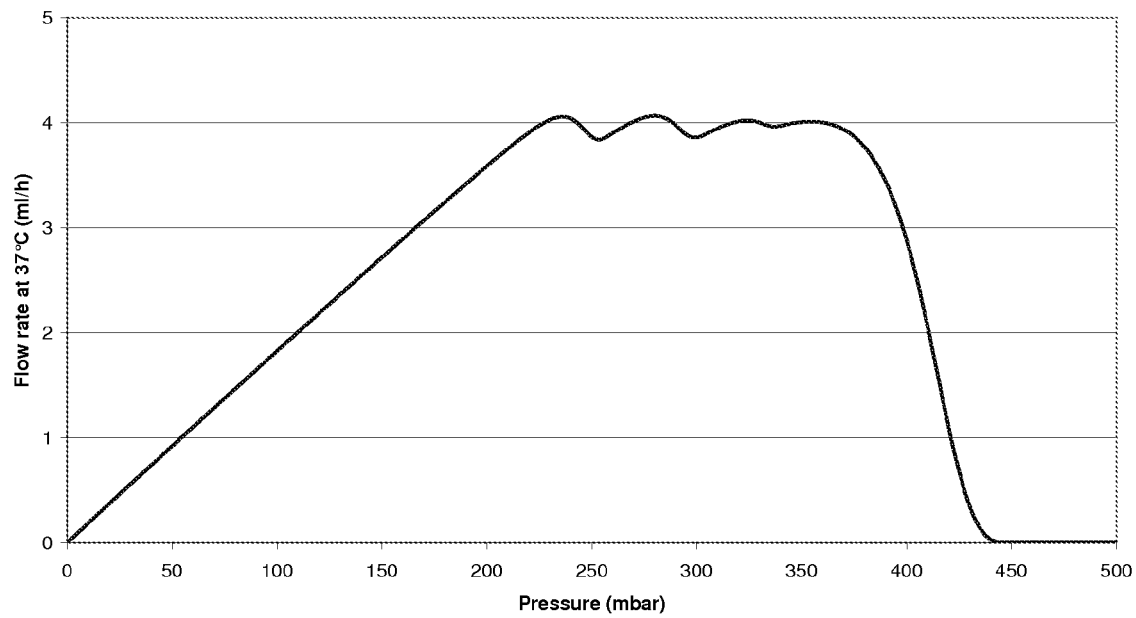

FIG. 16 shows the simulated flow rate versus pressure characteristic of a passive flow regulator having a silicon membrane according to the dimensions given in table 1.

Figure 17:
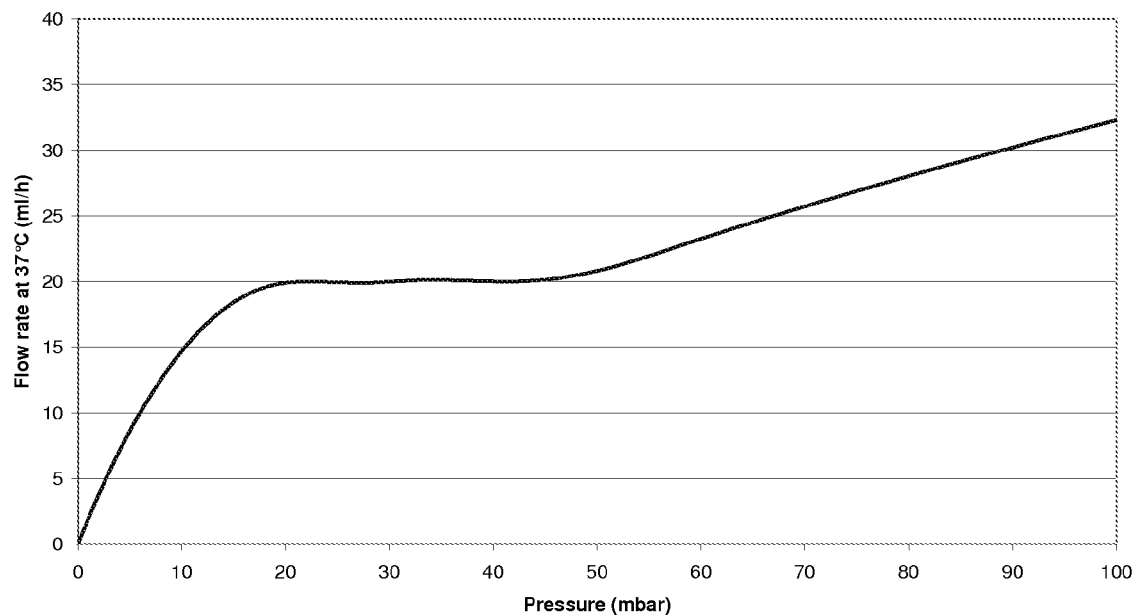

FIG. 17 shows the simulated flow rate versus pressure characteristic of a passive flow regulator having a silicon membrane according to the dimensions given in table 2.

Figure 18:
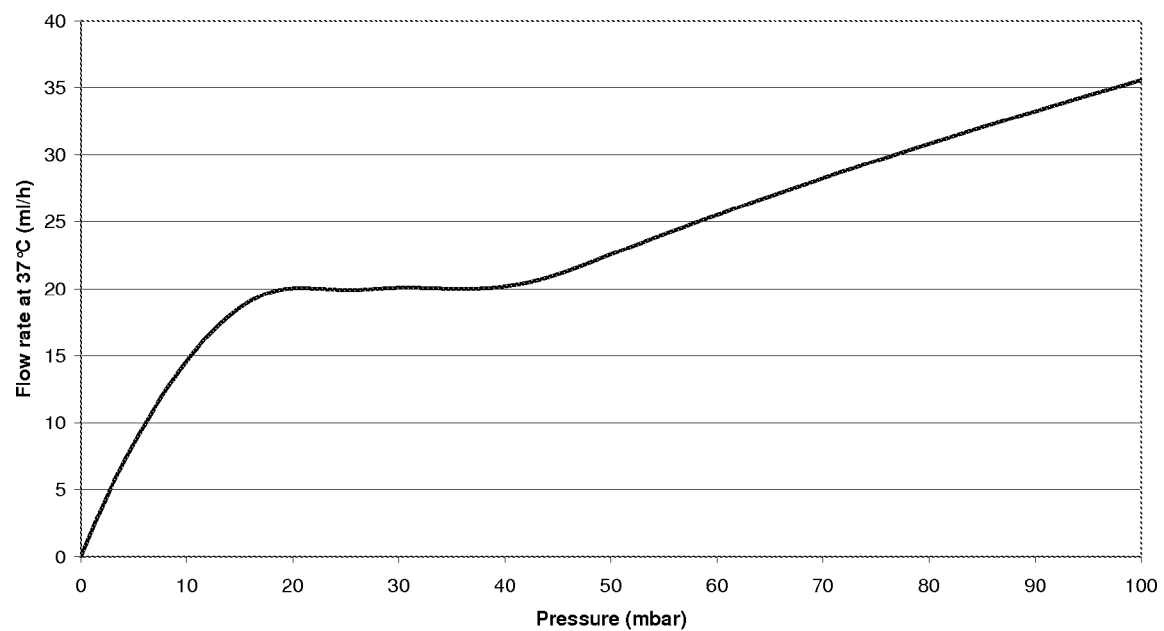

FIG. 18 shows the simulated flow rate versus pressure characteristic of a passive flow regulator having a PMMA membrane according to the dimensions given in table 3.

In a first preferred embodiment of the invention, the device is made of a stack of 2 plates:
⇨ A top layer with a flexible membrane 1 (called hereafter membrane)
⇨ A middle plate 2 with pillars 4 having through holes 11, cavity 5, inlet ports 9 and outlet port 10 (called hereafter pillar plate)

Figure 1A:
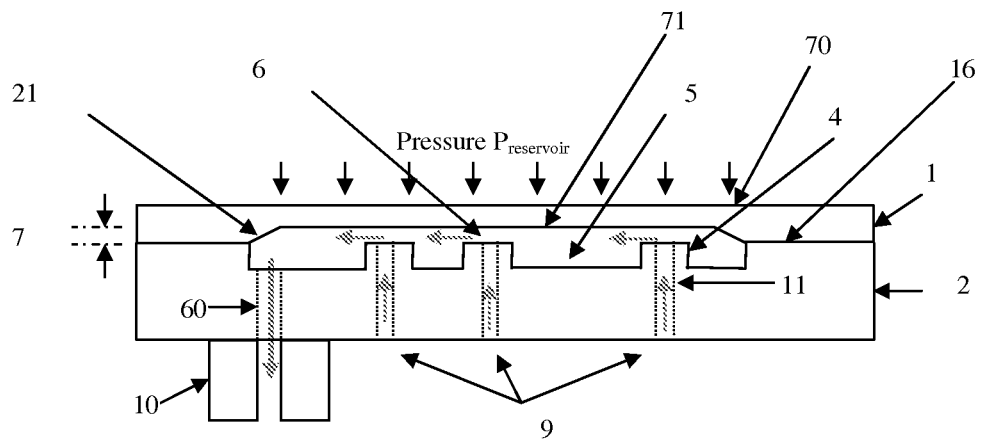
FIG. 1a shows a simplified cross-sectional view of a fluid flow regulator according to the first preferred embodiment of the present invention, wherein the through holes are machined in the pillars.

A simplified side view of the device is shown in FIG. 1a (not at scale).

As for all side views of the present invention, the direction of the flow is indicated by gray arrows.

Principle of the Device According to the First Embodiment of the Present Invention:

The pillar plate 2 is tightly linked to the membrane 1 in predefined linking areas 16.

The membrane 1 has two sides: the front side of the membrane 70 (upper surface) is submitted to the pressure of the fluid reservoir not represented in FIG. 1a whilst the back side of the membrane 71 is located within a recess 21 in front of the pillar plate. The recess 21 of the membrane is connected to a cavity 5 in the pillar plate 2. The pillar plate 2 contains pillars 4 having through holes 11, said pillars being surrounding by the cavity 5 which is connected to a large outlet through hole 60 and an outlet port 10. The cavity 5 is therefore submitted to the outlet pressure except in front of the pillar. By design, the pillar areas 4 should be at least 10 times smaller that the areas of the cavity 5.

When the membrane is at rest position, i.e. when there is no pressure in the fluid, the membrane back side 71 in front of the pillar 4 forms a valve 6 having an initial gap 7. The valve 6, made of the annular fluidic restriction between the membrane back-side 71 and the top of the pillar 4, has an inlet (through hole 11) and an outlet (cavity 5).

FIG. 1a shows a fluidic pathway (gray arrows) that is made of the inlet ports 9, the through holes 11 in the pillar plate 2, the valve 6, the cavity 5, the outlet through hole 60 and finally the outlet port 10.

The inlet ports 9 are connected to the reservoir at the pressure $P_{reservoir}$ and the outlet through hole 60 and outlet port 10 are connected to the delivery location at the pressure $P_{out}$.

The pressure reservoir induces a flow according to said fluidic pathway. Because the opening of the valve 6 (equal to the initial gap without pressure) depends on the reservoir pressure since by increasing the reservoir pressure, the membrane 1 moves towards the pillars 4 of the pillar plate 2, obstructing gradually the through holes 11 of the pillars 4 and therefore closing gradually the valves 6, the fluidic resistance of the valve depends on the pressure. Except the fluidic resistance of the cavity which depends also on the pressure because its heigth depends on the membrane deflection and therefore on the reservoir pressure, all other parts of the fluidic pathway show constant fluidic resistances.

The operating principle of the device imposes that the fluidic resistance of the inward part of the fluidic pathway (respectively between the inlet port 9 and the valve 6) is at least ten times larger that the fluidic resistance of the downward part of the fluidic pathway (that comprises the cavity, the outlet through hole 60 and the outlet port 10). The obvious corollary is that the fluidic resistance of the cavity, which depends on reservoir pressure, should be at least ten times smaller that the fluidic resistance of the inward fluidic pathway whatever the reservoir pressure.

In a first approximation, the flexible part of the membrane is therefore submitted to a gradient of pressure equal to the difference between the reservoir pressure and the outlet pressure.

Any change of the reservoir pressure induces a change of the valve opening and therefore to their fluidic resistances. For such annular valves, and according to the discussion in the state of the art paragraph, the fluidic resistance of such valves is not linear but varies as the power of −3 with their opening height. The use of only one valve is not sufficient to offer the possibility of the constant flow rate or any specific flow profile when the reservoir pressure changes.

To get a constant flow rate over a given range of pressure, it is necessary to implement at least two valves that are closed gradually but not at the same rate when increases the reservoir pressure. In practice, the valve located near the centre of the membrane 1 will be closed first while the valves located near the edge of the membrane need higher pressures to shut off. The diameters of the through holes 11, the positions of the pillars 4, the diameter and thickness of the membrane 1 and finally the height of the cavity 21 are chosen to obtain a constant flow rate over a specified range of pressure.

As a general trend, the higher the number of valves the better the flow accuracy.

In a second preferred embodiment of the invention, the device is made of a stack of 2 plates:
⇨ A top layer with a flexible membrane 1 having through holes 208
⇨ A middle plate 2 with full pillars 4, cavity 5, inlet ports 9 and outlet port 10
⇨

Figure 1B:
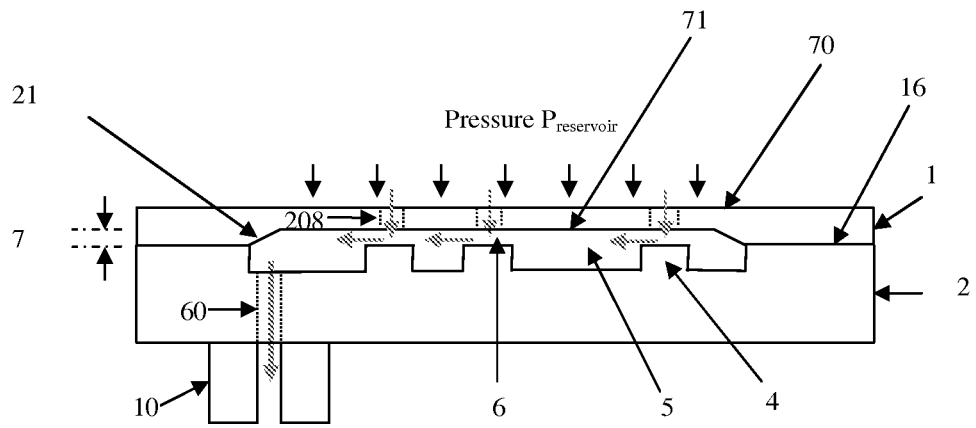
FIG. 1b shows a simplified cross-sectional view of a fluid flow regulator according to the second preferred embodiment of the present invention, wherein the through holes are machined in the membrane.

A simplified side view of the device is shown in FIG. 1b (not at scale).

The fluid of the reservoir is in contact with the upper surface 70 of the membrane 1. The pressure in the reservoir induces a flow through the through holes 208, the valve 6, the cavity 5 and finally the outlet through hole 60 and the outlet port 10. The operating principle is very similar to the first preferred embodiment of the present invention: any change of the reservoir pressure modifies the opening of the valves 6 and therefore their fluidic resistances. The holes in the membrane have a fluidic resistance at least ten times larger than any other part of the fluidic pathway when the membrane is at rest position (no pressure in the reservoir). The device may be designed to ensure that the fluidic resistance remains constant over a specified range of pressure.

To form a valve 6, the full pillars 4 are machined in front of the though holes 208 of the membrane 1. Depending on the regulation profile deisred, typically if a free flow at large pressure is needed, one or several through holes 208 may be located in front a the cavity 5 wherein there is no pillar. Pillars are not systematically placed in front of a hole, typically when there is a need to have a support for the membrane at high pressure or when the dead volume of the device should be optimized.

In order to ensure a very low flow rate regulation, typically few milliliters per day or less, the through holes 11 in the pillar 4 or the through holes 208 in the membrane 1 should have diameters of few microns. Because the relative machining tolerances for such tiny holes is large using MEMS processes or plastic injection, the final accuracy of the device is bad. There is a need to another regulator design for low flow regulation. The later design will be based on the first preferred embodiment of the present invention.

In another embodiment of the invention, the device dedicated to low flow rate is made of a stack of 3 plates:
⇨ A top layer with a flexible membrane 1
⇨ A middle plate 2 with pillars 4, through holes 11 and eventually channels 8
⇨ A bottom substrate 3 with fluidic ports 9 and 10 and eventually channels 8 (hereafter called bottom substrate)

Figure 2A:
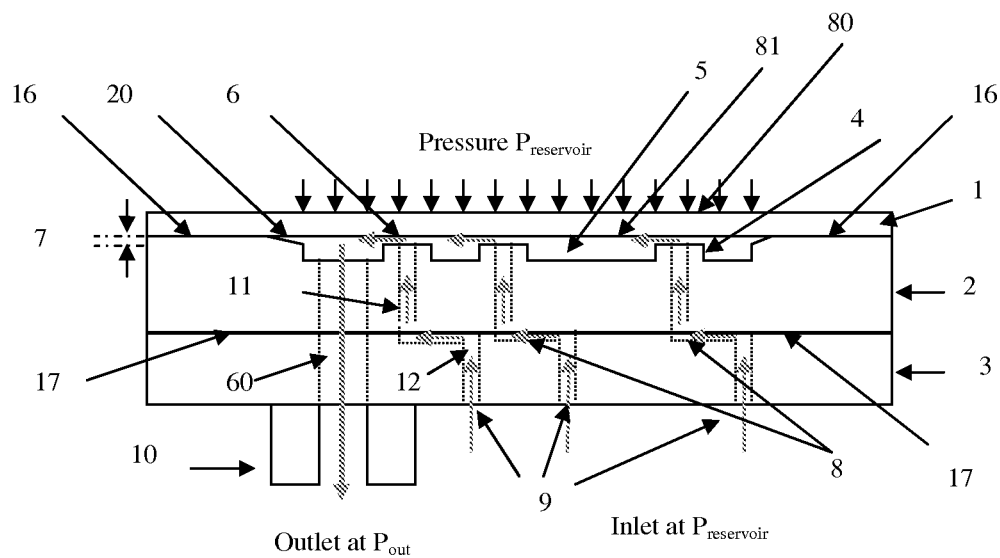
FIG. 2a shows a simplified cross-sectional view of a fluid flow regulator according to another embodiment of the present invention, wherein the membrane is flat and wherein the channels are machined into the bottom plate.

A simplified side view of the device is shown in FIG. 2a (not at scale).

Principle of the Device According to this Another Embodiment of the Present Invention Dedicated to Low Flow Rate:

The pillar plate 2 is tightly linked to the membrane 1 and the bottom plate 3 in predefined linking areas 16 and 17 respectively. The cavity 5 between the membrane and the pillar plate has a large outlet through hole 60 compared to the other through holes in order to ensure that the pressure within the cavity is very close to the outlet pressure.

The membrane 1 has two sides: the front side of the membrane 80 (upper surface) is submitted to the pressure of the fluid reservoir not represented in FIG. 2a whilst the back side of the membrane 81 (lower surface in front of the cavity 5 and pillars 4) is submitted to the outlet pressure except in front of the pillar. By design, the pillar areas 4 should be at least 10 times smaller that the areas of the cavity 5.

When the membrane is at rest position, i.e. when there is no pressure in the fluid, the membrane back side 81 in front of the pillar 7 forms a valve 6 having an initial gap 7. The valve 6, made of the annular fluidic restriction between 81 and 4, has an inlet (through holes 11) and an outlet (cavity 5).

FIG. 2a shows a fluidic pathway (gray arrows) that is made of the inlet ports 9, the through holes 12 in the bottom plate, the channels 8 between the bottom plate and the pillar plate, the through holes 11 in the pillar plate, the valve 6, the cavity 5, the outlet through hole 60 and finally the outlet port 10.

The inlet ports 9 are connected to the reservoir at the pressure $P_{reservoir}$ and the outlet through hole 60 and outlet port 10 are connected to the delivery location at the pressure $P_{out}$.

The pressure reservoir induces a flow according to said fluidic pathway. Because the opening of the valve 6 (equal to the initial gap without pressure) depends on the reservoir pressure since by increasing the reservoir pressure, the membrane 1 moves towards the pillars 4 of the middle plate 2, obstructing gradually the through holes 11 of the pillars 4 and therefore closing gradually the valve 6, the fluidic resistance of the valve depends on the pressure. Except the fluidic resistance of the cavity which depends also on the pressure because its heigth depends on the membrane deflection and therefore on the reservoir pressure, all other parts of the fluidic pathway show constant fluidic resistances.

The operting principle of the device imposes that the fluidic resistance of the inward part of the fluidic pathway (respectively between the inlet port 9 and the valve 6) is at least ten times larger that the fluidic resistance of the downward part of the fluidic pathway (that comprises the cavity, the outlet through hole 60 and the outlet port 10). The obvious corollary is that the fluidic resistance of the cavity, which depends on reservoir pressure, should be at least ten times smaller that the fluidic resistance of the inward fluidic pathway whatever the reservoir pressure.

In a first approximation, the flexible part of the membrane is therefore submitted to a gradient of pressure equal to the difference between the reservoir pressure and the outlet pressure.

Any change of the reservoir pressure induces a change of the valve opening and therefore to their fluidic resistances. For such annular valves, and according to the discussion in the state of the art paragraph, the fluidic resistance of such valves is not linear but varies as the power of −3 with their opening height. The use of only one valve is not sufficient to offer the possibility of the constant flow rate or any specific flow profile when the reservoir pressure changes.

To get a constant flow rate over a given range of pressure, it is necessary to implement at least two valves that are closed gradually but not at the same rate when increases the reservoir pressure. In practice, the valve located near the center of the membrane will be closed first while the valves located near the edge of the membrane need higher pressures to shut off.

The presence of at least two passive valves having variables fluidic resistances as varies the reservoir pressure is the main feature of the present invention. The first and second preferred embodiments of the present invention illustrates two differents ways to obtain such passive valves.

The regulating range of pressure of the device is defined by the behavior of the valves and their sensibility to pressure.

The range of flow rate depends on the fluidic resistance of the inward fluidic pathway between the reservoir and the valve 6. Large fluidic resistances are required to obtain small flow rate.

The channels 8 are the second major feature of the present invention as depicted FIG. 2a: because these channels are decoupled to the valves themselves, they can be as long or as tight as necessary to reach high fluidic resistances.

The stress limiters 130 and/or 131 are the third major features of the present invention as depicted FIGS. 10 and 12: because the stress in the membrane is limited at high pressure, it is not necessary to use only a material having a very high yield strength like silicon: the use of metal or hard plastic is made possible by these stress limiters, inducing a significant reduction of the cost of the device.

In the two preferred embodiments of the present invention, the direction of the flow in the inlet ports 9 and outlet ports 10 is perpendicular to the membrane plane as shown FIG. 1b.

Figure 2B:
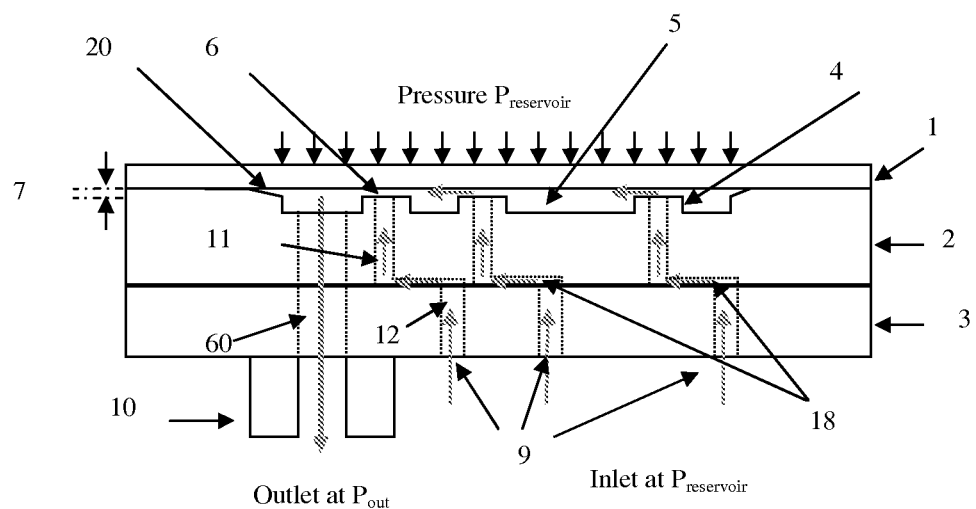
FIG. 2b shows a simplified cross-sectional view of a fluid flow regulator according to another embodiment of the present invention, wherein the channels are machined into the pillar plate.

As shown FIG. 2b, the channels 18 can be made in the pillar plate 14 and in that case, the bottom substrate 3 is simply made of a flat plate with through holes 12.

Figure 2C:
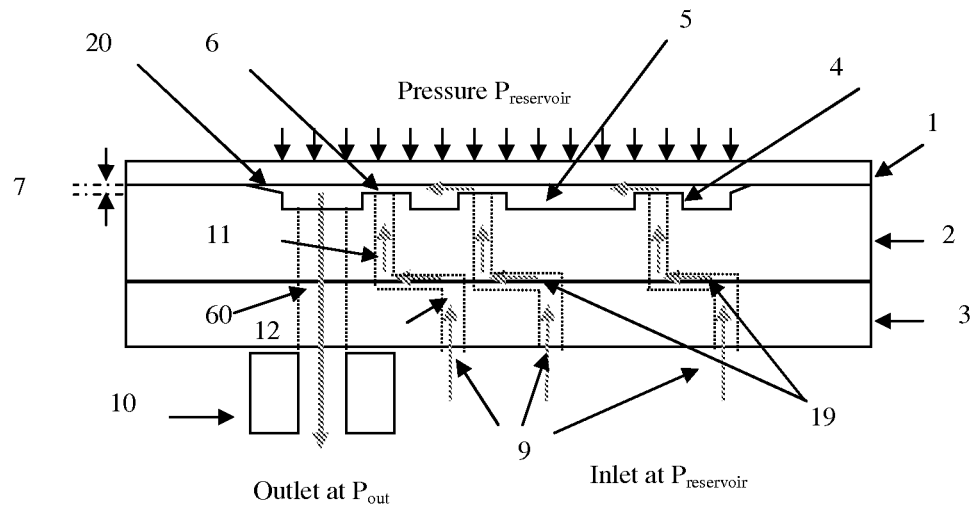
FIG. 2c shows a simplified cross-sectional view of a fluid flow regulator according to another embodiment of the present invention, wherein the channels are machined into both bottom and pillar plates.
Figure 3:
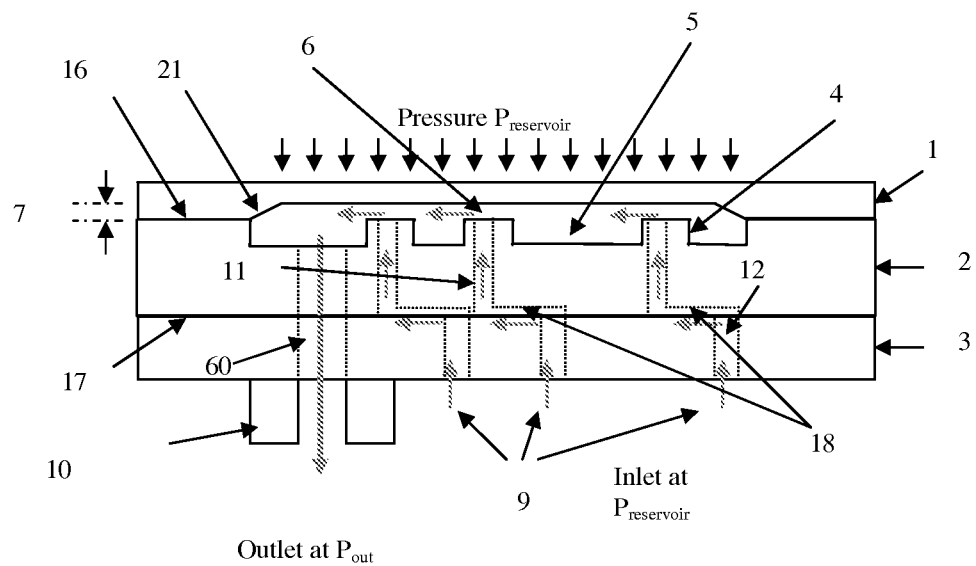
FIG. 3 shows a simplified cross-sectional view of a fluid flow regulator according to another embodiment of the present invention, wherein the membrane is etched to form a recess.

As shown FIG. 2c, the channels 19 can be made in both pillar plate 2 and bottom plate 3.

A recess cavity 21 is etched in the membrane 1 as shown in FIG. 1a and 1b while the recess cavity 20 is made by etching the pillar plate 2 as shown in FIGS. 2a and 2b.

The height of the recess cavity 20 or 21 defines the gap 7.

Except the outlet, the whole device can be connected to the pressurized fluid. A thin protective membrane 34 (see FIG. 4a), typically a polymeric film, can be deposited onto the top surface of the membrane 1 in order to prevent a free flow after the breaking of the membrane.

The pillar plate 2 and the bottom plate 3 can be made either in Pyrex or in silicon or in other materials including ceramic, plastic or metal.

Channels 8 and/or 18 and/or 19 are typically made of V-grooves obtained by KOH etching of silicon substrate.

Channels 8 and/or 18 and/or 19 can be machined or directly obtained during embossing or injection.

Channels 8 and/or 18 and/or 19 are not limited to one street.

The through holes 208, 11, 12 and 60 can be obtained by dry etching, sand blasting, ultrasonic drilling or any other suitable technique.

The device can include means for measuring the deflection of the membrane 1, typically by implanting strain gauges into the silicon membrane in a Wheatstone bridge configuration.

The critical parts that need a special care in terms of machining tolerances are the membrane 1 thickness and flatness, the through holes 208 diameters, the gap 7 and the channel depths 8, 18 and 19.

Since the pressure in the pillar cavity 4 should be very close to the outlet pressure, the fluidic resistance of the outlet including eventual tubing or catheter should be ideally at least an order of magnitude lower than the other parts of the device independently of the functioning pressure.

The cross-section of the channels 8, 18 and 19 is typically triangular, rectangular or trapezoidal depending of the process used, but there is in fact no restriction for the cross-section shape.

There is at least one channel.

Each pillar 4 through hole can be connected to the same channel 8, 18 and 19.

The typical device has at least one channel 8, 18 and 19 for each pillar 4.

The channels 8, 18 or 19 should exhibit the main fluidic restriction of the device when the membrane 1 is not deflected. By increasing the pressure above the membrane 1, the resistance of each valve 6 increases up to becoming larger than the resistance of the channel 8, 18 or 19 at a predefined pressure value for each valve 6.

Figure 4A:
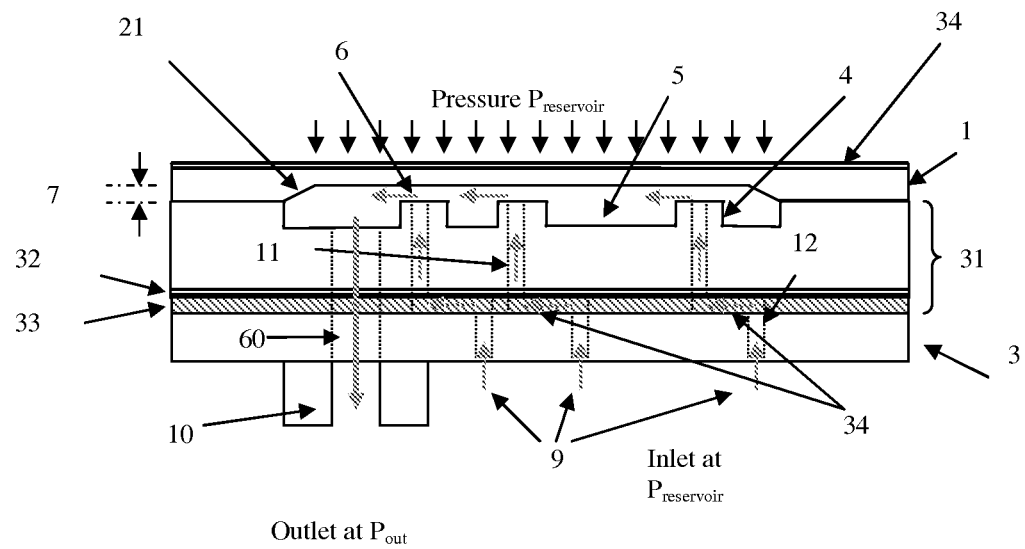
FIG. 4a shows a first simplified cross-sectional view of a fluid flow regulator according to another embodiment of the present invention, wherein the channels are machined into the SOI layer of the pillar plate and wherein the recess is machined in the membrane.

The pillar substrate 31 may also include channel(s) 34, typically by using a Silicon-On-Insulator (SOI) wafer as shown in FIG. 4a. The oxide 32 is used as an etch stop during the machining of the channel in the SOI layer 33.

The use of SOI for the pillar substrate can be desirable to improve the channel depth machining accuracy because the oxide is a very efficient etch stop.

FIG. 4a shows a first simplified view of the third embodiment of flow regulator based on a SOI pillar plate 31.

Figure 4B:
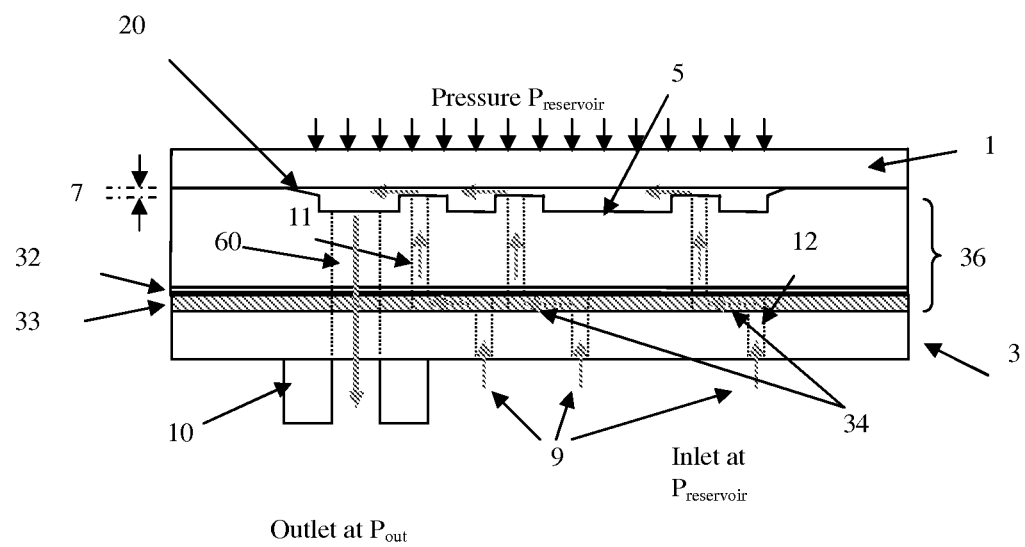
FIG. 4b shows a second simplified cross-sectional view of a fluid flow regulator according to another embodiment of the present invention, wherein the channels are machined into the SOI layer of the pillar plate and wherein the recess is machined in the pillar plate.

Depending on the process yield, all the critical parts may be included into the pillar plate 36 as shown FIG. 4b (e.g. SOI design shown hereafter with the recess 20 etched in the pillar plate 36). The membrane 1 is a simple flat plate without any machining while the bottom plates 3 is another simple flat plate only drilled in order to make the inlet through holes 12. The outlet port 10 could be a connector attached by any means including gluing to the bottom plate 3.

Figure 4C:
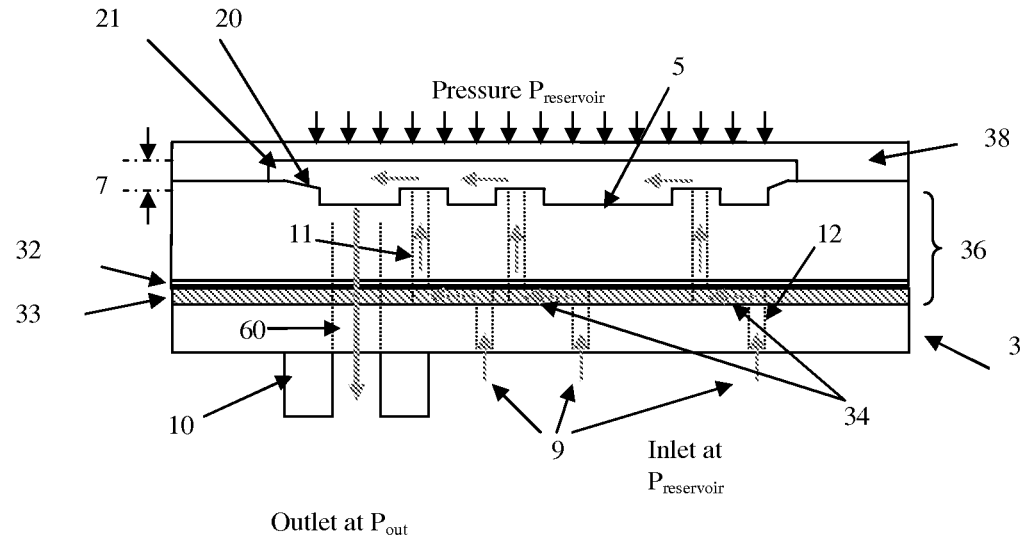
FIG. 4c shows a third simplified cross-sectional view of a fluid flow regulator according to another embodiment of the present invention, wherein the channels are machined into the SOI layer of the pillar plate and wherein the recess is machined in both the membrane and the pillar plate.

FIG. 4c shows a third simplified view of the third embodiment of the present invention, wherein both membrane 38 and pillar plates 36 are machined to create the gap 7.

Figure 4D:
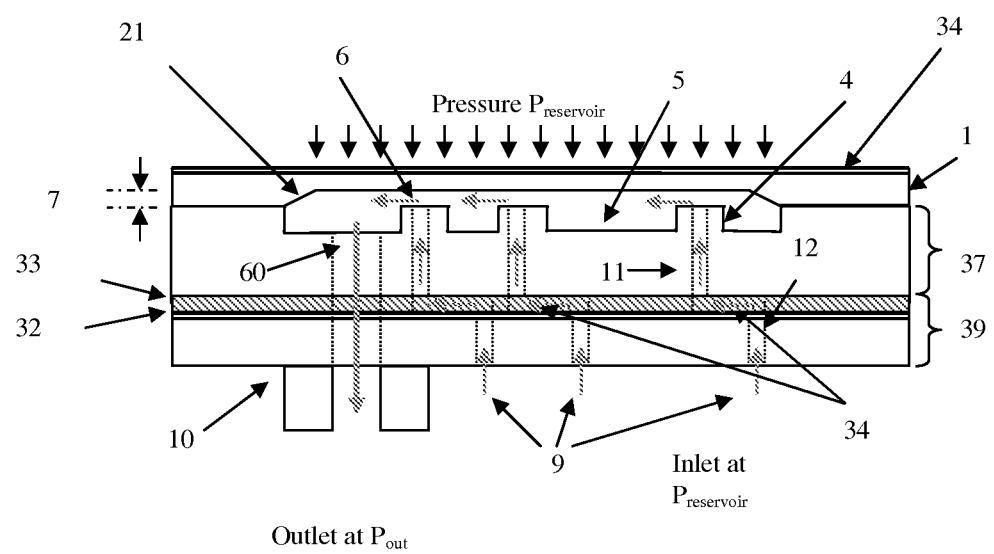
FIG. 4d shows a fourth simplified cross-sectional view of a fluid flow regulator according to another embodiment of the present invention, wherein the channels are machined into the SOI layer of the bottom plate and wherein the recess is machined in the membrane plate.

The pillar plate 37 may also contain no critical part as shown in FIG. 4d. The channel may be obtained by using again by using an SOI wafer for the bottom plate 39.

In another embodiment the device is only made of two plates, the membrane 1 and the pillar plate 2, and flow restrictors 46 (channels for instance) are placed into dedicated chips connected to the pillar plate 2 using tubing 44, connectors 47 or other fluidic routing. This another embodiment may increase the dead volume (and therefore the priming duration) and the complexity of the assembly. The main advantage is the possibility to use commercial off-the-shelf flow restrictors which can be easily tested before assembly. Each restrictor can be simply made of tubing having a small internal diameter 48. Each restrictor can be made using the same gauge of tubing by simply adjusting its length to reach to targeted resistance.

As for the second preferred embodiment of the present invention, the fluidic resistances of the through holes 11 in the pillar plate can also be adjusted so as to ensure a flow regulation in the expected range of pressure.

FIG. 5 represents a cross-section of device according to this another embodiment of the present invention, comprising a membrane 1 having a recess 21, a pillar plate 2 with through holes 11 and inlet connectors 47. Three different types of flow restrictors are also illustrated in FIG. 5, respectively flow restrictors communicating 46 with the through hole 11 of the pillar plate 2 using tubing 44, a flow restrictor directly made in the pillar plate (through hole 11 itself), and finally a flow restrictor made of tubing 48 of small internal diameter.

The plates are linked together at specified linking areas 16 and 17, typically by anodic bonding (for Pyrex and silicon plates), by direct bonding (for silicon plates), by Au—Au thermo-compression or by any other suitable bonding technique.

An anti-bonding layer 51 may be deposited or grown, outside of the linking areas, onto the membrane 1 backside. An anti-bonding layer 52 can be also made onto the pillar plate 2 front side.

The FIG. 6a shows a valve 6 according to the preferred embodiment of the present invention, wherein the anti-bonding layer is on the membrane 1 back-side. The shape of the anti-bonding layer 51 is made to limit the squeeze film effect, which occurs when two flat surfaces go into contact. The anti-bonding layer 51 is preferably made of small dimensions pads equally distributed over the whole surface of the membrane 1 (as shown FIG. 6a) or the pillar plate 2 (as shown FIG. 6b) or both. A specific anti-bonding shape 53 should be made for the valve 6 in order to cover the entire valve seat.

Additional features for any of the previous embodiments of flow regulator:
Specific coating of the surfaces in contact with the liquid, typically the membrane surfaces 80 and 81 or 70 and 71, the cavity 5 more generally the whole fluidic pathway, to prevent any corrosion of acid or basic solutions (e.g. $TiO_2$, ...)
Coating of hydrophilic agents onto all surfaces in contact with the liquid for better priming and lower surface contamination of the device (e.g. PEG ...)
Particle filter at the inlet to prevent valve leakage A typical front view of a channel 8 of the preferred embodiment of the present invention is illustrated FIG. 7a. This front view can correspond to the bottom plate 3 front-side as shown FIG. 2a or the pillar plate 2 back-side as shown FIG. 2b.

An inlet port 55 and an outlet port 56 are used to connect the channel 8 or 18 to the through holes 11 and 12 of the pillar and bottom plate respectively. The dimensions of the ports 55 and 56 are mainly driven by the alignment tolerances of the bonding process. The tight connection should be ensured and the alignment should not affect the fluidic resistance of the channel 8 or 18.

An example of a pillar plate front view 2 according to the preferred embodiment of the present invention is shown FIG. 7b. The position of the outlet 60 with respect to the pillars 4 is mainly driven by the resistance of the fluidic pathway between the pillars and the outlet which should be small with respect to other resistances. According to this remark, the outlet 60 should be ideally placed near the pillar 4, which is linked to the channel 8 that shows the largest flow restriction.

The maximum distance between each pillar 4 (with or without through hole) is driven by the effect of the secondary deformation of the freestanding part of the membrane 1 between those pillars at high pressure. This additional deformation should not modify the fluidic behaviour of the device.

The pillar cavity 5 shown in the FIG. 7b should be designed by considering the two former remarks, but also by considering the priming capability of the device. The pillar cavity geometry will ideally minimize the dead volume and ensure that the main stream travels through the largest part of this dead volume.

There is no limitation for the external shape of the device.

In another embodiment, the present invention concerns a flow regulator of the passive type comprising a fluid inlet 9 adapted to be connected to a fluid reservoir and a fluid outlet 10 adapted to be connected to a delivery location, said regulator comprising a pillar plate 101, a bottom plate 3 and a membrane plate 100 having a recess 104 to define a flexible membrane 110, these three plates being tightly linked together in predefined linking areas 17 and 16 so as to define at least one cavity 5 and channels 8 therebetween, said cavity 5 being connected to said fluid outlet 10 by the through hole 60.

In this another embodiment of the present invention, said rigid substrate 101 has a first surface opposite to said cavity 5 which is connected to said fluid inlet 9 and while said membrane 100 has an external surface opposite said cavity 5, said pillar plate 101 furthermore having at least a through hole 11, said bottom plate having a channel 8 and a through hole 12 contiguous with said through hole 11, to define a pathway for a fluid from said fluid inlet 9 to said fluid outlet 10, said flexible membrane 110 being able to come into contact with said pillar 4, of the pillar plate 101 within said cavity 5 and with a portion including said through hole 11 and defining a valve 6, in case a fluid applies a pressure on said external surface that is larger than a first predefined threshold value, which results in hindering a fluid from flowing through said through hole 11 and said valve 6, wherein said pillar plate comprises at least one additional through hole 114 in an additional cavity 115 contiguous to said cavity 5, wherein the fluid can flow from said additional cavity 115 toward the cavity 5 via openings 120, wherein said membrane plate 100 comprises at least an additional flexible membrane 111, said additional flexible membrane being able to come into contact with said pillar plate 101 onto the pillar 117, within said additional cavity 115 and with a portion including said additional through hole 114 and defining an additional valve 116, in case a fluid applies a pressure on said external surface that is larger than said first predefined threshold value but smaller than a second predefined threshold value, said additional membrane 111, said additional cavity 115 and said additional through hole 114 being further arranged so that a fluid flow rate is be substantially linear as a function of the pressure applied on said external surface in a range going approximately from said first to said second predefined threshold values.

A simplified side-view of this another embodiment of the present invention is shown FIG. 8a, the regulator undergoing a first low pressure. The same regulator undergoing a second higher pressure is illustrated FIG. 8b.

A simplified pillar plate front view of one of the fifth embodiment is shown FIG. 9a.

The membrane back-side (etched side) of this another embodiment is shown FIG. 9b. Depending on the process used, the recess 104 or 105 may have a recess wall showing a slope. By using anisotropic wet etch on <100> silicon wafer, the typical recess wall angle is 54.7°.

The different cavities in the device should be interconnected as shown FIG. 9a with the openings 120. Ideally, the fluidic resistances of these interconnections are designed to ensure that the pressure in all cavities is very close to the outlet pressure.

The membrane plate 100 can include membranes of any shape including squared, rectangular, elliptical and circular membrane. Membrane of different shapes can be made in the same membrane plate 100.

In the two preferred embodiments of the present invention, the deformation of the membrane 1 against a pillar plate 2 is used. This effect is strongly non-linear, resulting in a stiffening of the membrane 1 by increasing pressure. To close a non-centred valve 6, a large pressure and/or a wide and/or a thin membrane 1 is necessary. Valves can be classified as low and high-pressure valves, i.e. a valve that is closed at low (resp. high) pressure.

In the embodiment of the present invention depicted FIG. 8a, the pillars 4 are placed in front of the center of the membranes 110. In that later configuration, the threshold is adjusted, from one valve to another in the same membrane plate 100, by the dimension of the membrane and the distance between the membrane and the substrate. The high-pressure valves of the first embodiment are replaced, e.g., by valves having smaller membrane surface and/or thicker membranes. To reduce the dimension of the low pressure membrane, the gap 7 (the depth of each recess cavity 104 in the membrane plate 100) is smaller than the membrane thickness.

In the preferred embodiments, reducing the gap 7 makes the contact radius of the membrane 1 on the pillar plate 101 increasing very quickly at low pressure, and therefore central part of the membrane 1 is only used to regulate a small range of low pressure. This explains why the pillars 4 are significantly decentred by design.

The design of the embodiment depiected FIG. 8a allows a larger range of operating pressures and a better accuracy over the whole range because high-pressure and low-pressure valves can be embedded into the same device. It is however important to take care of the physical integrity of the low-pressure valve at high reservoir pressure: the yield strength of the material should not be reached otherwise plastic deformation will be observed, leading to a change of the fluidic behaviour of the device.

The membrane of the preferred embodiments is preferably made of silicon, first of all because of its very high yield strength but also because MEMS techniques allow good machining tolerances for the through holes and channels. There is a strong interest of using a cheaper membrane material like plastic: for cost reason by also for the simplification of the process and the possibility to make in a simplified manner membranes having different thicknesses and gap having different heights.

The embodiment depicted FIG. 8a, which can be made in plastic, would be made of:
⇨ A non-drilled membrane plate 100
⇨ A pillar plate 101 having large through holes 11, pillars 130 and steps 131 for the limitation of the membrane 100 stress at high pressure
⇨ A channel plate 3 having through holes 12 and channels 8.

As for the preferred embodiments of the present invention, the number and the dimension of the valves are adjusted to match the required accuracy and flow regulated pressure range.

The concepts of stress limiter pillars 130 and steps 131 (SLP/SLS) are illustrated FIG. 10 hat shows a valve 6 of the fifth embodiment of the present invention. The valve 6 comprises here both stress limiters, but in a preferred embodiment, only one type of stress limiter is used, typically the step because the dead volume of the device is smaller. Only one valve 6 is shown FIG. 10 for sake of clarity; the device can include several valves depending of the range of pressure. The centre of the membrane 100 reaches first the pillar 4 with the through hole 11 and closes the valve 6. By increasing the reservoir pressure, the membrane 100 goes into contact with the stress limiter step 131 and/or the pillar 130 or both. The additional bending of the membrane is limited thanks to this mechanical support. By using pillars 130 instead of steps 131, openings 135 should be included to avoid air trapping. The SLP should therefore not have the perfect cylindrical symmetry as shown FIG. 11.

The SLP 130 or SLS 131 or both are positioned and designed to ensure that the yield strength of the membrane material is not reached during the functioning of the device. Several steps or pillars may be used.

The SLP 130 or SLS 131 have typically a height larger than the pillar 4 having the through hole 11.

The channel 18 is preferably included into the pillar plate. The channels 18, the pillars 4 and 30, the steps 131 and all parts of the plastic plates should respect the standard design rules of molding or embossing (adapted clearance angles . . . ).

In another embodiment of the present invention, the SLP 145, the valve pillar 145 and the cavity 150 are machined in the membrane backside 140 as shown FIG. 12. The pillar plate 142 has no longer pillar but still through holes 11 (also named through holes in the text).

Gluing, soldering, fusion bonding or any other bonding techniques can be used to assemble the different plates using the predefined linking areas 16 and 17. The plates can be made of different materials, for instance the membrane 1 or 100 or 140 could be made of silicon while the pillar plate 2 or 101 or 142 and the bottom plate 3 are made of plastic. Any combination of material can be considered. The compatibility between these materials and the fluid to be injected should be considered. The water absorption of the materials should not affect the fluidic behaviour of the device, typically if plastic materials are used.

An another embodiment of the present invention is depicted FIG. 13a. This embodiment is directly derived from the second preferred embodiment of the present invention, wherein there are additional steps 131.

This another embodiment comprises therefore at least two plates:
⇨ A membrane plate 1 having at least two through holes 208
⇨ A pillar plate 2 having an outlet through hole 60, pillars 4 and steps 131.

A simplified view of a valve 6 of this another embodiment is shown FIG. 13a.

By placing another pillar plate 222 above the drilled membrane 1, it is possible to make a bidirectionnal flow regulator. The FIG. 13b illustrates a bidirectional valve made of two valves 6 and 230. Another embodiment of the present invention comprises at least 2 bidirectional valves.

The number of valves is adjusted by design to meet the accuracy budget of the device, the range of pressure and the device dimensions. The bidirectionnal flow regulator shown FIG. 13b is symmetric.

The FIG. 13c illustrates a simplified view of asymmetric valves 6 and 237 as an element of another embodiment of the present invention. The valve 237 is a check-valve with a pillar 229 placed in a cavity 261 which is connected to the pressurized reservoir via the through hole 200 in the plate 222. The pillars 229, which may have an anti-bonding layer 233, are here in contact with the membrane when the reservoir is not pressurized.

Depending of the height of the pillar 223 and the anti-bonding layer thickness it is possible at adjust the threshold of the check-valve 237.

Any of the previous embodiments can advantageously include a switch that allows selecting externally the channels 8 in order to change the flow rate. The switch can be made, for instance, of a polymeric layer 310 with openings 311 and a hole for the inlet 312. By rotating and pushing the film 310 against the bottom plate 300, some channels 8 become open while other ones become closed.

The FIG. 14a illustrates the corresponding backside of the bottom plate with three series of aligned through holes 302, 303 and 304 respectively. Each series of through holes can be seen as an individual regulator. We can consider for instance that the three series of through holes 302, 303 and 304 corresponds to three regulators having nominal flow rates of 1, 2 and 4 ml per hour respectively. The outlet 301 of the bottom plate 300 will be preferably located at the centre of the film 310 for symmetry evidence. The channels are located here at the interface between the pillar plate 2 and the bottom plate 3. For embodiments having no bottom plate, the FIG. 14a corresponds to the backside of the pillar plate 2.

The FIG. 14b illustrates a film 310 with radial openings 311 (slits) and opening 312 (hole) at its centre.

The film 310 can be assembled on the bottom plate 300 using mechanical clamps, screws, clips or other standard assembly means. For the embodiments only made of a membrane and a pillar plates, the film is directly applied on the pillar plate.

For the fourth embodiment of the present invention that is only made of a membrane and a pillar plates, the film is directly applied on the pillar plate.

For the seventh embodiment of the present invention that is only made of a drilled membrane and a pillar plates, the film is directly applied on the membrane plate.

The FIG. 14c shows the film 310 aligned with the bottom plate 300 to let all through holes 302, 303 and 304 opened. In the later configuration, the total flow rate is the sum of the nominal flow rate of the three series of through holes. According to the former example, the flow rate is therefore 7 ml per hour. By rotating the film, the total flow rate can be set to 1 to 7 ml per hour by combination of the three nominal flow rates. The arrows 320 around the film indicate the position of the film that leads to the required flow rate.

Considering any of the preceding embodiments comprising at least one hole in a pillar or a membrane that is not intended to be closed at high pressure, the outlet shall be located very close to said hole in order to reduce first the fluidic resistance but also to prevent the presence of any residual bubble that should block said hole.

Because the different embodiments of the device are intended first to regulated rather low flow rate (typically few ml per hour), the priming capability of the devices is a major concern. The design shall minimize the air trapping area wherein the flow rate is very small. The dead volume (typically the cavity 5) shall be also optimized as shown FIG. 7b wherein the cavity 5 is limited to the area surrounding the holes of the fluidic pathway.

The device can advantageously include a protective cap and a fluidic switch as depicted FIGS. 15a and 15b in order to reduce the priming duration. The embodiment depicted FIG. 2a, which is one of the preferred embodiments for low flow rate regulation, has been used to illustrates these new features.

The protective cap 440, made in a hard material, e.g. Pyrex™ or silicon, is tightly linked to the surface 80 of the membrane 1 in predefined linking areas 430 having the same layout that the linking areas 16. The protective cap 440 has a cavity 441 above the flexible part of the membrane 1 except on pillars 443 wherein an antibonding layer 442 is made to prevent any bonding between the pillars and the membrane 1. The pillars are in contact with the membrane and therefore only the displacement of the membrane towards the pillar substrate is possible. The protective cap has at least one fluidic port 444 which is connected to the cavity 441 because the pillars 443 are not in contact between each others. Only two pillars are shown FIGS. 15a and 15b but there is no limitation on the number or the shape or the disposition of the pillars.

The fluidic port 444 is connected to the reservoir of the device via a fluidic pathway made of a fluidic line 412, a fluidic switch 420 and a fluidic line 411 between the reservoir and the switch.

The inlet ports 9 of the device are connected to the reservoir via another fluidic pathway made of a fluidic line 413, a fluidic switch 420 and a fluidic line 411 between the reservoir and the switch.

In FIG. 15a the switch is placed in position 1 which corresponds to the priming position: the reservoir is filled and the pressure rises up to $P_{reservoir}$. The fluid can flow from the reservoir to the device via the line 413 while the line 412 and the cavity 441 of the protective cap are not pressurized. The membrane does not deflect towards the pillar and all valves 6 are open even at high pressure, inducing a high flow rate in the device and therefore faster priming. The pillars 443 prevent the breaking of the membrane when too large pressure is applied in the reservoir when the switch is in position 1. When the priming is finished (when the fluid flows at the outlet 10), the switch is turned in position 2 which corresponds to the infusion position as shown FIG. 15b. The reservoir pressure is not present both at the inlet ports 9 and the cavity 441, and the device can now regulate the flow according to its intended use.

In order to reduce the priming duration, a syringe (not represented here) can be used to generate the high priming pressure: the syringe can be plugged directly onto the switch in position 1 and the user can then prime the device by pressing onto the syringe plunger. The syringe should then be removed and replaced by the reservoir.

The switch may include other positions, for instance a pressure release position to vent the lines 412 and 143 or a position that isolates the reservoir from both inlet ports 9 and protective cap 440 (not represented in FIGS. 15a and 15b).

Any of the previous embodiments can advantageously include at least an active valve. The active valve can be made of an actuator linked permanently to the membrane or simply during the actuation. The valve may include a conductive or magnetic layer to that end. Various types of actuators can be used:
- ⇒ Piezo
- ⇒ Electrostatic
- ⇒ Shape Memory Alloy
- ⇒ Shape Memory Polymer
- ⇒ Electromagnetic . . . .

The active valve can be used to regulate the flow (duty cycle mode) or simply as a safety valve that closes or opens the valve under predefined conditions. To that end, the active valve may be advantageously connected to a pressure or flow rate sensor.

Nonrestrictive examples of regulation profiles are given below for the preferred embodiment of the present invention:
- ⇒ Constant flow rate in a predefined range of pressure.
- ⇒ An opening threshold at low pressure, a constant flow rate in an intermediate range of pressure and a shut-off at high pressure.
- ⇒ Hydrocephalus like profile having an opening threshold at low pressure, a constant flow rate in an intermediate range of pressure and a free flow at high pressure.

The preferred embodiment of the present invention is based on the elastic deformation of a flexible membrane. FEM simulations are necessary to estimate the shape of the membrane at the different functioning pressures.

The pillars (drilled or not) support the deflected membrane. A correct repartition of the pillars ensures an axi-symmetric deformation of the pressurized membrane.

Model for the Preferred Embodiment of the Present Invention:

We consider a device as depicted in FIG. 2a. Basically, there are two main fluidic restrictions in the device:
1. The channels.
2. The valves.

All other parts of the fluidic pathways should be negligible in term of fluidic resistance by design. The pillar cavity is therefore designed to meet this requirement as well as the through holes and outlet diameters.

Notations:
Dynamic viscosity of the fluid $\eta$
Fluid volumetric mass $\rho$
Young modulus E
Membrane thickness $t_m$
Hole radius $R_h$
Hole depth $L_h$
Pillar radius $R_p$
Distance between the pillar i and the membrane (valve opening height): $h_i$
Pressure gradient $\Delta P = P_{in} - P_{out}$
Flow rate via the fluidic pathway i: $Q_i$
Channel width $w_c$
Channel height $h_c$
Channel length $L_c$
Fluidic resistance $R_f$
Fluidic resistance of a channel $R_{fc}$
Fluidic resistance of a valve $R_{fv}$
Fluidic resistance of the outlet $Rf_{out}$ The flow can be modelled as fluidic resistances in series for the channel and the valve, each couple of channel and valve being placed in parallel between each other (same inlet and same outlet). We assume the flow is laminar.

Rectangular channels are considered here. The fluidic resistance $R_{f_i}$ of the channel i is:

$$R_{fc_i} = \frac{12\eta L_{ci}}{w_c h_c^3 \left[1 - \frac{192 h_c}{\pi^5 w_c} \sum_{j=1,3,5,\ldots}^{\infty} \frac{\tanh(j\pi w_c / 2h_c)}{j^5}\right]}$$

For $w_c \gg h_c$ (flat channel):

$$R_{fc_i} = \frac{12\eta L_{ci}}{w_c h_c^3}$$

Fluidic resistance $Rfv_i$ of the valve i:

$$Rfv_i = \frac{6\eta}{\pi h_i^3} \ln\left(\frac{R_p}{R_h}\right)$$

The flow rate Q takes the form:

$$Q = \sum_i Q_i = \Delta P \sum_i \frac{1}{Rfc_i + Rfv_i}$$

If the Reynolds number become much larger than one at the given pressure, the singular head losses shall be considered.

Singular head losses are proportional to the square of the flow rate and therefore we should consider them at high flow rate. It is important to note that the reversibility of the flow is no longer valid. We should consider the fluidic pathway in both directions.

The difference of pressure $\Delta P = P_{in} - P_{out}$ is written as a function of $Q_i$ as follow:

$$\Delta P = \alpha_i Q_i^2 + \beta_i Q_i$$

Where i indicates one fluidic pathway, $$\beta_i = \sum_i Rf_i$$

is the sum of the fluidic resistance of the fluidic pathway I and $\alpha_i$ is a function of the surfaces of each singularity.

We estimate numerically the function $\alpha_i Q_i$ for each value of $\Delta P$:

$$\alpha_i Q_i = -\frac{\beta_i}{2} + \sqrt{\alpha_i \Delta P + \frac{\beta_i^2}{4}}$$

The total flow rate is therefore:

$$Q = \sum_i Q_i$$

To simplify the formulation, we consider that the channels 8 have the shape of a hole. We consider in the general case all contributions to the fluidic resistances including outlet through hole 60 and cavities 5. For positive gradient of pressure, the fluid flows therefore through the channel 8 (here a hole), the valve 6, the cavity 5 which is assimilated to a fluidic channel and finally the outlet through hole 60 (having also the shape of a hole), the parameters $\alpha_i$ and $\beta_i$ take the form:

$$\begin{cases} \alpha_i = \frac{\rho}{2}\left(\frac{1.4}{\pi^2 R_{hi}^4} + \frac{1}{4\pi^2 h_i^2 R_{pi}^2}\left(1 - \frac{h_i}{h_c}\right)^2 + \xi_i\right) \\ \beta_i = \frac{8\eta L_{hi}}{\pi R_{hi}^4} + \frac{6\eta}{\pi h_i^3}\ln\left(\frac{R_{hi}}{R_{pi}}\right) + \frac{12\eta L_{ci}}{w_{ci} h_{ci}^3} \\ \xi_i \frac{1}{\pi^2 R_{hi}^4}\left(1 - \frac{R_{hi}}{2h_i}\right)^2 \text{ if } R_h \leq 2h_i \\ \xi_i = \frac{1}{10\pi^2 h_i^2 R_{hi}^2}\left(1 - \frac{2h_i}{R_{hi}}\right) \text{ if } R_h \geq 2h_i \end{cases}$$

For negative gradient of pressure, i.e. when the fluid flows through the outlet through hole 60, the cavity 5 (channel) up to the valve 6 and finally the channel 8 (hole), the parameters $\alpha$ and $\beta$ take the form:

$$\begin{cases} \alpha_i = \frac{\rho}{2}\left(\frac{1}{10\pi^2 h_i^2 R_{pi}^2}\left(1 - \frac{h_i}{h_c}\right) + \frac{1}{4\pi^2 h_i^2 R_{pi}^2} + \frac{1}{\pi^2 R_{hi}^4} + \xi_i\right) = \\ \frac{\rho}{2}\left(\frac{1}{4\pi^2 h_i^2 R_{pi}^2} + \left(1.4 - \frac{h_i}{h_c}\right) + \frac{1}{\pi^2 R_{hi}^4} + \xi_i\right) \\ \beta_i = \frac{8\eta L_{hi}}{\pi R_{hi}^4} + \frac{6\eta}{\pi h_i^3}\ln\left(\frac{R_{hi}}{R_{pi}}\right) + \frac{12\eta L_{ci}}{w_{ci} h_{ci}^3} \\ \xi_i \frac{0.4}{\pi^2 R_{hi}^4}\left(1 - \frac{R_{hi}}{2h_i}\right) \text{ if } R_h \leq 2h_i \\ \xi_i = \frac{1}{4\pi^2 h_i^2 R_{hi}^2}\left(1 - \frac{2h_i}{R_{hi}}\right)^2 \text{ if } R_h \geq 2h_i \end{cases}$$

We consider also a fluidic resistance at the outlet $Rf_{out}$ (e.g. the infusion line). In that case, for a given pressure gradient $\Delta P$, we estimate the flow rate Q as shown previously. The additional pressure drop $\Delta P_{out}$ due to $Rf_{out}$ is then:

$$\Delta P_{out} = Rf_{out} Q$$

The effective gradient of pressure necessary to get the flow rate Q is therefore:

$$\Delta P_{eff} = \Delta P + \Delta P_{out}$$

The functions $h_i(P)$ are estimated using the FEM model for the membrane deformation under pressure.

A detailed description of the embodiment depicted FIG. 9*a* (multimembrane design) is provided here. We assume the gap is no larger than 0.4 times the width of the membrane. In that configuration the deflection up to the contact is linear with pressure.

An analytical model is used to estimate the flow rate versus pressure characteristic of the device.

To simplify the formula of the membrane deflection under pressure, we design a device having pillar plate and a membrane plate made of circular membrane and circular holes.

The flow can be modelled using simply fluidic resistances in series including the holes and the opening between the pillars and the membrane.

The distance $h_i(P)$ between the membrane centre i and the pillar i at the pressure P (opening height of the valve i) is:

$$h_i(P) = h(P_0) - \frac{P r_{mi}^4}{64D}$$

With $$D = \frac{E t_m^3}{12(1-v^2)}$$

For $P < P_{contact\,i}$, where $P_{contact\,i}$ is the contact pressure of the membrane i against the pillar i, $h(P_0)$ is the initial gap height (=recess height), D is the plate constant, $r_{m\,i}$ the radius of the membrane i, $t_m$ the membrane thickness and $v$ the Poisson's ratio of the membrane material.

For $P > P_{contact\,i}$, $h_i(P) = 0$

Flow Regulation at 4 ml/Day for a 4-Membrane Silicon Regulator

The flow regulator can be used for pain management. Smaller flow rates are expected, typically 1 ml per hour or less. To avoid overdoses, the device should be a shut-off valve at high pressure.

A silicon device having four membranes and four channels have been used for the following simulation. Such valves without the features 130 and 131 are illustrated FIG. 10. The device may also be obtained using a single membrane with still several channels and several pillars below said membrane according the embodiment depicted FIG. 2*a* or 2*b* or 2*c*. In all cases the number of membranes or the number of pillars below the same membrane may be varied depending on the targeted flow rate and accuracy.

Device parameters:
- ⇨ Silicon membranes
- ⇨ Young modulus 170 GPa
- ⇨ Poisson coefficient 0.262
- ⇨ Thickness 50 microns
- ⇨ Gap 20 microns Channel parameters:
- ⇨ Depth 2.5 microns
- ⇨ Width 100 microns The dynamic viscosity is 0.0007 Pa.s at 37° C.

The channel lengths have been adjusted to match the flow rate of 4 ml per day between 200 and 400 mbar. The table 1 summarizes the main dimensions of the device:

TABLE 1 dimensions of a silicon regulator for drug infusion at 4 ml per day

| Diameter (mm) | Channel length (mm) | pillar diameter (um) |
|---|---|---|
| 5.43 | 1.97 | 300 |
| 5.81 | 23.9 | 300 |
| 5.98 | 15.02 | 300 |
| 6.23 | 9.48 | 300 |

FIG. 16 represents the simulated relationship between the flow rate and the pressure.

The main error on the flow rate accuracy for a flat channel is mainly due to the error on the depth. Using Silicon-On-Insulator, an error of −/−0.05 micron at 1σ (=+/−2% for a depth of 2.5 microns) can be achieved on the channel depth, leading to an error of about −/−6% at 1σ on the flow rate accuracy. The error due to the lateral etching of the channel is about +/−0.33% (100+/−0.33 microns at 1σ) and can be neglected.

The microchannels introduce here an error of −/−6% at 1σ on the flow rate accuracy.

For instance, the following specifications would apply for a flow regulator according to invention, which is embedded into an implantable pump for analgesics delivery:

a) Constant flow rate of 1 ml/day
b) Liquid equivalent to water in term of viscosity
c) Temperature=37° C.
d) Range of pressure=200 to 400 mbar The same device can be made using a membrane having holes in front of the pillars as depicted in FIG. 1b or 13a. To match the flow rate of 4 ml per day, using the two same membranes and gap of 20 microns, the holes should exhibit a diameter of respectively 6.81 um, 3.3 um, 4.3 um and 4.6 um. The very small dimensions of the holes indicate that this design is not well adapted to low flow rate because the machining tolerances of the holes limit strongly the flow rate accuracy of the device.

This example illustrates the interest of the embodiments of the present invention that comprise channels 8 or 18 or 19 to generate the flow restriction instead of tiny holes) for low flow rate regulation.

The flow regulators previously exposed can be embedded into an implantable pump that contains:

A titanium housing
A drug reservoir
Filling ports for the drug
A catheter port
A catheter access port for bolus injection
A pump drive
A temperature sensor
A flow regulator
A filter (e.g. bacterial filter with pore size of 0.22 micron)
A controlled valve
Batteries to power the valve, the temperature sensor and the pressure sensor
Wireless system to power the pressure sensor and the temperature sensor
Alarm system that indicates:
 Low batteries
 Empty drug reservoir
 Over or under pressures (out of the regulated pressure range)
 Membrane Break
 Overheating The flow regulator according to the present invention offers in particular the following advantages:

⇒ Lower risks of under and over dose due to pressure changes (climbing, diving . . . )
⇒ No risk of explosion if no gas propeller is used
⇒ Lower risk during the fill/refill procedure
⇒ No risk of overdose during impact to the body in the pump of the pump Flow Regulator for Hydrocephalus A device dedicated to hydrocephalus has been also designed in silicon (Young Modulus of 170 GPa and Poisson's ratio 0.262) and PMMA (Young Modulus of 3 GPa and Poisson's ratio 0.35).

The regulation profile has been set to regulate the flow rate at 20 ml/h between 15 and 40 mbar. The high flow rate makes possible the use of hole in the flexible membrane instead of a channel connected to a drilled pillar.

The device is therefore made of 2 plates in silicon or PMMA:

⇒ A membrane plate having 2 membranes having one hole at their centres; one membrane has also an additional hole near the edge of the membrane.
⇒ The outlet and the pillars are made in the bottom plate The fluid pressure directly applies on the top surface of the membrane. The pillars and the membranes have here the same dimensions for both designs.

For plastic device these dimensions may be variable inside the same regulator. Grey arrows indicate the flow direction. A valve of the later device according to the seventh embodiment of the present invention is illustrated FIG. 13a.

The critical dimensions of the silicon and PMMA devices are shown in the Table 2 and 3. The third hole is located on the edge of a membrane while the two other membrane holes are centred.

TABLE 2 dimensions of the silicon valve for hydrocephalus.

| Membrane diameter (um) | Membrane thickness (um) | Gap (um) | Hole diameter (um) | Pillar diameter (um) |
|---|---|---|---|---|
| 9250 | 50 | 20 | 69.5 (centre) | 166 |
| 10750 | 50 | 20 | 79 (centre) | 179 |
|  |  |  | 63.5 (edge) | 150 |

TABLE 3 dimensions of the PMMA valve for hydrocephalus.

| Membrane diameter (um) | Membrane thickness (um) | Gap (um) | Hole diameter (um) | Pillar diameter (um) |
|---|---|---|---|---|
| 3550 | 50 | 20 | 72 (center) | 145 |
| 4100 | 50 | 20 | 55 (center) | 100 |
|  |  |  | 67 (edge) | 150 |

The surface of the PMMA device is more than 6 times smaller than the similar device made of a single membrane in silicon.

The flow characteristics have been simulated and the graphs are shown in FIGS. 17 and 18 for the silicon and the PMMA devices respectively.

Depending on the mechanical, chemical and biocompatibility requirements, other plastic materials can be used like SAN, COC, PC . . . .

The invention is of course not limited to the above cited examples and related figures. There is for instance no limitation to the number and the distribution of the valves, through holes, pillars and the channels. The shapes of the pillars, stress limiter features, through holes, membranes and pads for the anti-bonding layer or channels are not limited to the above cited examples.

The invention claimed is:

1. Flow regulator comprising a fluid inlet adapted to be connected to a fluid reservoir and a fluid outlet adapted to be connected to a delivery location, said regulator comprising:
   a rigid substrate with a top surface and a bottom surface and a membrane comprising a top surface, a bottom surface and a flexible portion;
   wherein the top surface of the substrate is attached to the bottom surface of the membrane;
   said substrate and/or said membrane having:
   a recess so as to define, when said membrane is in a rest position, a cavity between said membrane and said substrate;
   a through hole contiguous with said cavity and communicating with said fluid outlet,
   at least two pillars within said cavity, the height of each of said pillars being such that, when said membrane is at rest, a gap is formed between the pillar free end and the opposite cavity wall;
   said regulator further comprising two additional through holes contiguous with said cavity and communicating with said fluid inlet wherein at least one of said additional holes is arranged in the substrate;
   wherein each of said pillars is furthermore aligned with one of said additional through holes and forming a valve in said gap and said pillars have furthermore a width that is larger than the width of said aligned through hole;
   wherein the fluid, which flows through said regulator, applies a pressure on the to surface of the membrane in such a way that said membrane is able to come into contact with:
   at least a first part of said substrate, within said cavity and with a portion including a first of said valves, in case a greater pressure than a first predefined threshold value is applied on the top surface of the membrane, which results in lowering said gap height up to zero and hindering a fluid from flowing through said first valve,
   at least a second part of said substrate, within said cavity and with a portion including a second of said valves, in case a pressure larger than a second predefined threshold value is applied on the top surface of the membrane, which results in hindering a fluid from flowing through said second valve; wherein the pillars and the additional through holes positions and dimensions are arranged so that the fluid flow rate is passively regulated at least in a range of pressure going from said first and said second predefined threshold values.

2. Flow regulator according to claim 1, comprising n additional pillars in said cavity, said substrate and/or said membrane comprising at least n additional though holes contiguous with said cavity, communicating with said fluid inlet, and forming n valves, each i-th valve being arranged such that the fluid may flow through it in case a pressure smaller than a i-th predefined threshold value is applied on the surface of the membrane opposite to the said substrate, said n valves being further designed and arranged so that the fluid flow rate is passively regulated at least in a range of inlet pressure going approximately from said first and said (n+2)-th predefined threshold values.

3. Flow regulator according to claim 1, comprising at least one flow restrictor which is communicating with at least one of said additional through holes of the substrate, wherein said flow restrictor has a fluidic resistance larger, in a predefined range of pressure, than the fluidic resistance of the other parts of the fluidic pathway.

4. Flow regulator according to claim 1, comprising a bottom plate tightly linked to the pillar plate in predefined linking areas, said bottom plate comprising through holes communicating with said additional through holes of the substrate and with the fluid inlet, defining a fluidic pathway from the inlet to the outlet made of the inlet connected to said fluid reservoir, said through holes in the bottom plate, said additional through holes in the substrate, said valve, said cavity and said through hole communicating with the outlet.

5. Flow regulator according to claim 4, wherein the interface between said substrate and said bottom plate contains a channel plane in which at least one channel is defined, said additional through holes of the substrate and said through holes of the bottom plate communicating via at least of said channel and wherein said channel has, in a predefined range of inlet pressure, a fluidic resistance larger than the fluidic resistances of the other parts of the fluidic pathway.

6. Flow regulator according to claim 5 wherein said interface between the substrate and the bottom layer is a layer of Silicon-on-Insulator.

7. Flow regulator according to claim 1, wherein at least one of said valve is a shut-off valve and/or a check-valve.

8. Flow regulator according to claim 1, wherein the linking areas between said membrane and said substrate defines m flexible parts of the membrane and m cavities between said m flexible parts of the membrane and said substrate, said m cavities being communicating between each other and with a common through hole connected to the outlet, each of said m cavities comprising at least one pillar, one through hole connected to the inlet and therefore at least one valve, each j-th valve being arranged such that the fluid may flow through it in case a pressure smaller than a j-th predefined threshold value is applied on the surface of the membrane opposite to the said substrate, said m valves being further designed and arranged so that the fluid flow rate is passively regulated at least in a range of inlet pressure going approximately from said first and said (m+2)-th predefined threshold values.

9. Flow regulator according to claim 8, wherein the thickness and/or the diameter or both of each said m flexible part of the said membrane and/or the height and the diameter or both of each of the m pillars and/or the height of said m cavities and/or the diameter of each m through holes are variable.

10. Flow regulator according to claim 1, comprising in said cavity at least one full pillar, i.e. devoid of any through hole, and/or at least one step, wherein said full pillar and/or said step are not forming part of a said valves, and wherein said pillar and for said step limit the deflection and the stress of the membrane in case a pressure larger than a predefined threshold value is applied.

11. Flow regulator according to claim 1, comprising an additional plate tightly linked to the membrane in predefined linking areas, wherein said additional plate and or membrane has recess to form a additional cavity between said membrane and said additional plate, said additional plate comprising a through hole connecting the pressurized reservoir to said additional cavity, wherein said additional plate comprises at least one pillar in front of said through holes in the membrane, said pillar closing said through hole in the membrane in a predefined range of pressure, preventing therefore a backflow in said through hole.

12. Flow regulator according to claim 1, comprising an additional plate tightly linked to the membrane in predefined linking areas, wherein said additional plate and or membrane has recess to form an additional cavity between said membrane and said additional plate, wherein said additional plate comprises at least one pillar that prevent the deflection of the membrane in the direction of said pillar, wherein said additional plate comprises a through hole connected to the said additional cavity, said flow regulator comprising a fluidic switch having at least three ports including a first port communicating with said fluid reservoir, a second port communicating with said through holes of the bottom substrate a third port communicating with said through hole in the additional plate, wherein the fluid flows only from the reservoir to the through holes of the bottom substrate when the switch is one a first position that allows the communication between the ports 1 and 2 while the port 3 is closed, preventing the application of the reservoir pressure in said cavity between said membrane and said additional plate and therefore the deflection of said membrane to close said valves, and wherein all ports of the switch are communicating between each other when the switch is in a second position, said additional cavity being therefore submitted to the reservoir pressure, allowing the fluid to flow from the reservoir to the through holes of the bottom substrate and allowing the displacement of the membrane and therefore the closure of the valves as varies the reservoir pressure.

13. Flow regulator according to claim 1, comprising a thin resilient polymeric layer above the surface of said membrane opposite to the said substrate.

14. Flow regulator according to claim 1, comprising a resilient and removable film on the bottom plate side opposite to the substrate and/or above the surface of said membrane opposite to the said substrate, said film having openings to selectively open or close one or several of said valves depending on the film positioning.

15. Flow regulator according to claim 1, wherein the membrane surface and/or the substrate surface within said cavity including said pillars comprise an anti-bonding layer.

16. Flow regulator according to claim 1, wherein the surfaces in contact with the fluid are coated with hydrophilic and/or anticorrosive agents.

17. Flow regulator according to claim 1, comprising an actuator adapted to exert pressure on said membrane.

18. Flow regulator according to claim 1, wherein said membrane comprises strain gauges.

19. Flow regulator according to claim 1, comprising a filter.

* * * * *